(12) United States Patent
Matsui et al.

(10) Patent No.: US 10,945,990 B2
(45) Date of Patent: Mar. 16, 2021

(54) COMBINATION OF A PD-1 ANTAGONIST AND ERIBULIN FOR TREATING CANCER

(71) Applicants: MERCK SHARP & DOHME CORP., Rahway, NJ (US); Eisai R&D Management Co., Ltd., Tokyo (JP)

(72) Inventors: Junji Matsui, Tsukuba (JP); Gursel Aktan, North Wales, PA (US); Vassiliki Karantza, Rahway, NJ (US); RuiRong Yuan, Fort Lee, NJ (US); Yasuhiro Funahashi, Tsukuba (JP); Erhan Berrak, River Vale, NJ (US)

(73) Assignees: EISAI R&D MANAGEMENT CO., LTD., Tokyo (JP); MERCK SHARP & DOHME CORP., Rahway, NJ (US)

(*) Notice: Subject to any disclaimer, the term of this patent is extended or adjusted under 35 U.S.C. 154(b) by 116 days.

(21) Appl. No.: 15/554,540

(22) PCT Filed: Mar. 3, 2016

(86) PCT No.: PCT/US2016/020734
§ 371 (c)(1),
(2) Date: Aug. 30, 2017

(87) PCT Pub. No.: WO2016/141209
PCT Pub. Date: Sep. 9, 2016

(65) Prior Publication Data
US 2018/0071247 A1 Mar. 15, 2018

Related U.S. Application Data

(60) Provisional application No. 62/128,373, filed on Mar. 4, 2015, provisional application No. 62/264,068, filed on Dec. 7, 2015.

(51) Int. Cl.
| | | |
|---|---|---|
| *A61K 31/357* | (2006.01) | |
| *A61K 45/06* | (2006.01) | |
| *A61K 39/395* | (2006.01) | |
| *A61K 9/00* | (2006.01) | |
| *C07K 16/28* | (2006.01) | |

(52) U.S. Cl.
CPC ......... *A61K 31/357* (2013.01); *A61K 9/0019* (2013.01); *A61K 39/39566* (2013.01); *A61K 45/06* (2013.01); *C07K 16/2818* (2013.01); *A61K 2300/00* (2013.01)

(58) Field of Classification Search
CPC .............. A61K 31/357; A61K 2300/00; A61K 2039/505; A61K 35/00; A61K 35/04
See application file for complete search history.

(56) References Cited

U.S. PATENT DOCUMENTS

| | | | |
|---|---|---|---|
| 6,214,865 B1 | 4/2001 | Littlefield et al. | |
| 7,488,802 B2 | 2/2009 | Collins et al. | |
| 7,521,051 B2 | 4/2009 | Collins et al. | |
| 7,982,060 B2 | 7/2011 | Austad et al. | |
| 8,008,449 B2 | 8/2011 | Korman et al. | |
| 8,093,410 B2 | 1/2012 | Chase et al. | |
| 8,168,757 B2 | 5/2012 | Finnefrock et al. | |
| 8,350,067 B2 | 1/2013 | Endo et al. | |
| 8,354,509 B2 | 1/2013 | Carven et al. | |
| 8,383,796 B2 | 2/2013 | Korman et al. | |
| 2011/0271358 A1 | 11/2011 | Freeman et al. | |
| 2015/0246033 A1* | 9/2015 | Flynn ................ A61K 31/4709 424/133.1 |

FOREIGN PATENT DOCUMENTS

| | | | |
|---|---|---|---|
| CN | 103562406 A | 2/2014 | |
| JP | 2002-518384 A | 6/2002 | |
| JP | 2006-340714 A | 12/2006 | |
| WO | WO-2004/004771 A1 | 1/2004 | |
| WO | WO-2004/056875 A1 | 7/2004 | |
| WO | WO-2004/072286 A1 | 8/2004 | |
| WO | WO-2007/061874 A2 | 5/2007 | |
| WO | WO-2008/156712 A1 | 12/2008 | |
| WO | WO-2010/027827 A2 | 3/2010 | |
| WO | WO-2010/077634 A1 | 7/2010 | |
| WO | WO-2011/066342 A2 | 6/2011 | |
| WO | WO-2012/135408 A1 | 10/2012 | |
| WO | WO-2013/019906 A9 | 3/2014 | |
| WO | WO-2014/087230 A1 | 6/2014 | |
| WO | WO-2014/159562 A1 | 10/2014 | |
| WO | WO-2014/193898 A1 | 12/2014 | |
| WO | WO-2014/208774 A1 | 12/2014 | |
| WO | WO-2014193898 A1 * | 12/2014 | ........... A61K 31/519 |
| WO | WO-2015/112900 A1 | 7/2015 | |
| WO | WO-2015/112900 A8 | 7/2015 | |
| WO | WO-2015/134605 A1 | 9/2015 | |
| WO | 2016/141209 A1 | 9/2016 | |

OTHER PUBLICATIONS

Cortes et al (Lancet, 2011, vol. 377, pp. 914-923) (Year: 2011).*
Study NCT01848834 (Archive for CinicalTrials.gov, Apr. 30, 2014) (Year: 2014).*
Pardoll (Nature Reviews Cancer, 2012, vol. 12, pp. 252-264) (Year: 2012).*
Devriese et al (Invest New Drugs, 2013, vol. 31, pp. 381-389) (Year: 2013).*
Knollman et al., "Muscle-invasive urothelial bladder cancer: an update on systemic therapy", Therapeutic Advances in Urology, vol. 7, No. 6, pp. 312-330 (Dec. 1, 2015).
International Search Report and Written Opinion dated Jan. 2, 2018 in PCT/US2017/056552.

(Continued)

*Primary Examiner* — Karen A. Canella
(74) *Attorney, Agent, or Firm* — Faegre Drinker Biddle & Reath LLP

(57) ABSTRACT

The present disclosure describes combination therapies comprising an antagonist of Programmed Death 1 receptor (PD-1) and eribulin or a pharmaceutically acceptable salt thereof, and the use of the combination therapies for the treatment of cancer.

6 Claims, 9 Drawing Sheets
Specification includes a Sequence Listing.

(56) References Cited

OTHER PUBLICATIONS

PCT/US2016/020734—International Preliminary Report on Patentability and Written Opinion dated Sep. 5, 2017.
Intellectual Property Office of Singapore, Written Opinion for Singaporean Patent Application No. 11201706872S, dated Jun. 27, 2018.
Ahmadzadeh M. et al., "Tumor antigen-specific CD8 T cells infiltrating the tumor express high levels of PD-1 and are functionally impaired," Blood (2009) 114: 1537-1544.
Dong H. et al., "Tumor-associated B7-H1 promotes T-cell apoptosis: A potential mechanism of immune evasion," Nat Med. Aug. 2002; 8(8): 793-800.
Eisai Public Relations Department: "Eisai and Merck Enter Collaboration to Explore Novel Combination Regimens of Anti-PD-1 Therapy with Multi-targeting RTK Inhibitor and Microtubule Dynamics in Multiple Types of Cancer," Mar. 4, 2015 URL:http//www.eisai.com/news/news201518.html.
Gao Q. et al., "Overexpression of PD-L1 Significantly Associates with Tumor Aggressiveness and Postoperative Recurrence in Human Hepatocellular Carcinoma," Clinical Cancer Research (2009) 15: 971-979.
Ghebeh H. et al., "The B7-H1 (PD-L1) T Lymphocyte-Inhibitory Molecule is Expressed in Breast Cancer Patients with Infiltrating Ductal Carcinoma: Correlation with Important High-Risk Propgnostic Factors," Neoplasia (2006) 8: 190-198.
Ghebeh H., "Foxp3+ $T_{regs}$ and B7-H1+/PD-1+ T lymphocytes co-infiltrate the tumor tissues of high-risk breast cancer patients: Implication for immunotherapy," BMC Cancer. Feb. 23, 2008; 8:57.
Hamanishi J. et al., "Programmed cell death 1 ligand 1 and tumor-infiltrating CD8+ T lymphocytes are prognostic factors of human ovarian cancer," Proceeding of the National Academy of Sciences (2007): 104: 3360-3365.
Hino R. et al., "Tumor Cell Expression of Programmed Cell Death-1 is a Prognostic Factor for Malignant Melanoma," Cancer (2010): 116: 1757-1766.
Inman B. et al., "PD-L1 (B7-H1) Expression by Urothelial Carcinoma of the Bladder and BCG-Induced Granulomata: Associations With Localized Stage Progression," Cancer (2007): 109: 1499-1505.
Nakanishi J. et al., "Overexpression of B7-H1 (PD-L1) significantly associates with tumor grade and postoperative prognosis in human urothelial cancers," Cancer Immunol. Immunother. (2007) 56: 1173-1182.
Nomi, T., et al., "Clinical Significance and Therapeutic Potential of the Programmed Death-1 Ligand/Programmed Death-1 Pathway in Human Pancreatic Cancer," Clinical Cancer Research (2007) ;13: 2151-2157.
Ohigashi Y. et al., "Clinical Significance of Programmed Death-1 Ligand-1 and Programmed Death-1 Ligand-2 Expression in Human Esophageal Cancer," Clin. Cancer Research (2005): 11: 2947-2953.
Sharpe, A.H, et al., "The function of programmed cell death 1 and its ligands in regulating autoimmunity and infection," Nature Immunology (2007); 8: 239-245.
Shimauchi T. et al., "Augmented expression of programmed death-1 in both neoplastic and non-neoplastic CD4+ T-cells in adult T-cell Leukemia/ Lymphoma," Int. J. Cancer (2007): 121: 2585-2590.
Thompson R. H. et al., "PD-1 is Expressed by Tumor-Infiltrating Immune cells and is Associated with Poor Outcome for Patients with Renal Cell Carcinoma," Clinical Cancer Research (2007) 13: 1757-1761.
Thompson R. H. et al., "Significance of B7-H1 Overexpression in Kidney Cancer," Clinical Genitourinary Cancer (2006): 5: 206-211.
WHO Drug Information, vol. 27, No. 1, pp. 68-69 (2013).
WHO Drug Information, vol. 27, No. 2, pp. 161-162 (2013).
Yang W. et al., "PD-1 Interaction Contributes to the Functional Suppression of T-Cell Responses to Human Uveal Melanoma Cells in Vitro," Invest Ophthalmol. Vis. Sci. Jun. 2008; 49(6 (2008): 49: 2518-2525.
International Search Report dated Apr. 28, 2016 for PCT/US2016/020734.
Written Opinion dated Apr. 28, 2016 for PCT/US2016/020734.
European Patent Office, Office Action for European Patent Application No. 16710891.9, dated Aug. 13, 2019.
Russian Patent Office, Office Action for Russian Patent Application No. 2017132877, dated Aug. 29, 2019.
Tolaney, S., et al., "Phase 1b/2 study to evaluate eribulin mesylate in combination with pembrolizumab in patients with metastatic triple-negative breast cancer," Eur. J. Cancer, 2017, 72: S16 [Abstract No. 177].
Nanda, R., "Pembrolizumab Shows Potential in Breast Cancer," Cancer Discovery, 2015, 5(2): 100-101.
The International Bureau of WIPO, International Preliminary Report on Patentability for International Application No. PCT/US2017/056552, dated Apr. 25, 2019.
Coates, A., et al., "Tailoring therapies—improving the management of early breast cancer: St Gallen International Expert Consensus on the Primary Therapy of Early Breast Cancer 2015," Annals of Oncology, 2015, 26(8): 1533-1546.
Jordan, M.A., et al., "The primary antimitotic mechanism of action of the synthetic halichondrin E7389 is suppression of microtubule growth," Mol. Cancer Ther., 2005, 4(7): 1086-1095.
Dybdal-Hargreaves, N., et al., "Eribulin Mesylate: Mechanism of Action of a Unique Microtubule-Targeting Agent," Clin. Cancer Res., 2015, 21(11): 2445-2452.
Twelves, C., et al., "Efficacy of eribulin in women with metastatic breast cancer: a pooled analysis of two phase 3 studies," Breast Cancer Res. Treat., 2014, 148: 553-561.
Adams, S., et al., "Phase 2 study of pembrolizumab as first-line therapy for PD-L1-positive metastatic triple-negative breast cancer (mTNBC): Preliminary data from KEYNOTE-086 cohort B.," Journal of Clinical Oncology, 2017, 35(15 suppl): 1088.
Adams, S., et al., "Phase 2 study of pembrolizumab (pembro) monotherapy for previously treated metastatic triple-negative breast cancer (mTNBC): KEYNOTE-086 cohort A.," Journal of Clinical Oncology, 2017, 35(15 suppl): 1008.
Cortes, J., et al., "Eribulin monotherapy versus treatment of physician's choice in patients with metastatic breast cancer (EMBRACE): a phase 3 open-label randomised study," Lancet, 2011, 377: 914-923.
Nanda, R., et al., "Pembrolizumab in Patients With Advanced Triple-Negative Breast Cancer: Phase Ib KEYNOTE-012 Study," Journal of Clinical Oncology, 2016, 34(21): 2460-2467.
Merck Sharp & Dohme Corp., Keytruda® Label, Suppl. 8, Oct. 2016, FDA Ref. ID: 4003165, available at: https://www.accessdata.fda.gov/drugsatfda_docs/label/2016/125514s008s012lbl.pdf.
Merck Sharp & Dohme Corp., KEYTRUDA® Label, Suppl. 9, Aug. 2016, FDA Ref. ID: 3968676, available at: https://www.accessdata.fda.gov/drugsatfda_docs/label/2016/125514s009lbl.pdf.
Cardoso, F., et al., "ESO-ESMO 2nd international consensus guidelines for advanced breast cancer (ABC2)," The Breast, 2014, 23: 489-502.
China National Intellectual Property Administration, First Office Action for Chinese Patent Application No. 201680025588.3, dated Jan. 6, 2020.
Japan Patent Office, Notice of Reasons for Rejection for Japanese Patent Application No. 2017-546075, dated Jan. 7, 2020.
Intellectual Property Office of Singapore, Second Written Opinion for Singaporean Patent Application No. 11201706872S, dated Nov. 5, 2019.
CTEP Rapid Communication, Solicitation for Letters of Intent: Clinical trials—Preclinical experiments, E7389, Halichondrin B analog (NSC 707389) (11 pages).
Asano, M., et al., "Broad-spectrum Preclinical Antitumor Activity of Eribulin (Halaven®): Combination with Anticancer Agents of Differing Mechanisms," Anticancer Research, 2018, 38: 3375-3385.
Yi, M., et al., "Biomarkers for predicting efficacy of PD-1/PD-L1 inhibitors," Molecular Cancer, 2018, 17: 129.
European Patent Office, Office Action for European Patent Application No. 16710891.9, dated Mar. 31, 2020.

(56) References Cited

OTHER PUBLICATIONS

Indian Patent Office, Office Action for Indian Patent Application No. 201747034283, dated Feb. 28, 2020.
Russian Patent Office, Office Action for Russian Patent Application No. 2017132877, dated Jan. 27, 2020.
Japanese Patent Office, Office Action for Japanese Patent Application No. 2017-546075, dated Jul. 21, 2020.
Chinese Patent Office, Office Action for Chinese Patent Application No. 201680025588.3, dated Jul. 7, 2020.
Mexican Patent Office, Office Action dated Nov. 24, 2020 in Mexican Patent Application No. MX/a/2017/011206 with partial English translation.
European Patent Office, Communication pursuant to Article 94(3) EPC dated Nov. 16, 2020 in European Patent Application No. 16 710 891.9.
Singapore Patent Office, Notice of Intention to Refuse Patent Application dated Nov. 19, 2020 in Singapore Patent Application No. 11201706872S.
Israeli Patent Office, Office Action for Israeli Patent Application No. 254133, dated Oct. 14, 2020 with partial English translation-characterization.

\* cited by examiner

```
hPD-1.08A light chain CDR1 (SEQ ID NO:1)
Arg Ala Ser Lys Ser Val Ser Thr Ser Gly Phe Ser Tyr Leu His hPD-1.08A light chain CDR2 (SEQ ID NO:2)
Leu Ala Ser Asn Leu Glu Ser hPD-1-08A light chain CDR3 (SEQ ID NO:3)
Gln His Ser Trp Glu Leu Pro Leu Thr hPD-1.08A heavy chain CDR1 (SEQ ID NO:4)
Ser Tyr Tyr Leu Tyr hPD-1.08A heavy chain CDR2 (SEQ ID NO:5)
Gly Val Asn Pro Ser Asn Gly Gly Thr Asn Phe Ser Glu Lys Phe Lys Ser hPD-1.08A heavy chain CDR3 (SEQ ID NO:6)
Arg Asp Ser Asn Tyr Asp Gly Gly Phe Asp Tyr
```

Figure 1 hPD-1.09A light chain CDR1 (SEQ ID NO:7)
Arg Ala Ser Lys Gly Val Ser Thr Ser Gly Tyr Ser Tyr Leu His hPD-1.09A light chain CDR2 (SEQ ID NO:8)
Leu Ala Ser Tyr Leu Glu Ser hPD-1.09A light chain CDR3 (SEQ ID NO:9)
Gln His Ser Arg Asp Leu Pro Leu Thr hPD-1.09A heavy chain CDR1 (SEQ ID NO:10)
Asn Tyr Tyr Met Tyr hPD-1.09A heavy chain CDR2 (SEQ ID NO:11)
Gly Ile Asn Pro Ser Asn Gly Gly Thr Asn Phe Asn Glu Lys Phe Lys Asn hPD-1.09A heavy chain CDR3 (SEQ ID NO:12)
Arg Asp Tyr Arg Phe Asp Met Gly Phe Asp Tyr

Figure 2

109A-H heavy chain variable region (SEQ ID NO:13)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser

409A-H heavy chain full length (SEQ ID NO:14)

Gln Val Gln Leu Val Gln Ser Gly Val Glu Val Lys Lys Pro Gly Ala Ser Val Lys
Val Ser Cys Lys Ala Ser Gly Tyr Thr Phe Thr Asn Tyr Tyr Met Tyr Trp Val Arg
Gln Ala Pro Gly Gln Gly Leu Glu Trp Met Gly Gly Ile Asn Pro Ser Asn Gly Gly
Thr Asn Phe Asn Glu Lys Phe Lys Asn Arg Val Thr Leu Thr Thr Asp Ser Ser Thr
Thr Thr Ala Tyr Met Glu Leu Lys Ser Leu Gln Phe Asp Asp Thr Ala Val Tyr Tyr
Cys Ala Arg Arg Asp Tyr Arg Phe Asp Met Gly Phe Asp Tyr Trp Gly Gln Gly Thr
Thr Val Thr Val Ser Ser Ala Ser Thr Lys Gly Pro Ser Val Phe Pro Leu Ala Pro
Cys Ser Arg Ser Thr Ser Glu Ser Thr Ala Ala Leu Gly Cys Leu Val Lys Asp Tyr
Phe Pro Glu Pro Val Thr Val Ser Trp Asn Ser Gly Ala Leu Thr Ser Gly Val His
Thr Phe Pro Ala Val Leu Gln Ser Ser Gly Leu Tyr Ser Leu Ser Ser Val Val Thr
Val Pro Ser Ser Ser Leu Gly Thr Lys Thr Tyr Thr Cys Asn Val Asp His Lys Pro
Ser Asn Thr Lys Val Asp Lys Arg Val Glu Ser Lys Tyr Gly Pro Pro Cys Pro Pro
Cys Pro Ala Pro Glu Phe Leu Gly Gly Pro Ser Val Phe Leu Phe Pro Pro Lys Pro
Lys Asp Thr Leu Met Ile Ser Arg Thr Pro Glu Val Thr Cys Val Val Val Asp Val
Ser Gln Glu Asp Pro Glu Val Gln Phe Asn Trp Tyr Val Asp Gly Val Glu Val His
Asn Ala Lys Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys Cys Lys Val
Ser Asn Lys Gly Leu Pro Ser Ser Ile Glu Lys Thr Ile Ser Lys Ala Lys Gly Gln
Pro Arg Glu Pro Gln Val Tyr Thr Leu Pro Pro Ser Gln Glu Glu Met Thr Lys Asn
Gln Val Ser Leu Thr Cys Leu Val Lys Gly Phe Tyr Pro Ser Asp Ile Ala Val Glu
Trp Glu Ser Asn Gly Gln Pro Glu Asn Asn Tyr Lys Thr Thr Pro Pro Val Leu Asp
Ser Asp Gly Ser Phe Phe Leu Tyr Ser Arg Leu Thr Val Asp Lys Ser Arg Trp Gln
Glu Gly Asn Val Phe Ser Cys Ser Val Met His Glu Ala Leu His Asn His Tyr Thr
Gln Lys Ser Leu Ser Leu Ser Leu Gly Lys

Figure 3

K09A-L-11 light chain variable region (SEQ ID NO:15)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys

K09A-L-16 light chain variable region (SEQ ID NO:16)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys

K09A-L-17 light chain variable region (SEQ ID NO:17)

Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys

Figure 4

K09A-L-11 light chain full length (SEQ ID NO:18)

Glu Ile Val Leu Thr Gln Ser Pro Ala Thr Leu Ser Leu Ser Pro Gly Glu Arg Ala
Thr Leu Ser Cys Arg Ala Ser Lys Gly Val Ser Thr Ser Gly Tyr Ser Tyr Leu His
Trp Tyr Gln Gln Lys Pro Gly Gln Ala Pro Arg Leu Leu Ile Tyr Leu Ala Ser Tyr
Leu Glu Ser Gly Val Pro Ala Arg Phe Ser Gly Ser Gly Ser Gly Thr Asp Phe Thr
Leu Thr Ile Ser Ser Leu Glu Pro Glu Asp Phe Ala Val Tyr Tyr Cys Gln His Ser
Arg Asp Leu Pro Leu Thr Phe Gly Gly Gly Thr Lys Val Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

K09A-L-16 light chain full length (SEQ ID NO:19)

Glu Ile Val Leu Thr Gln Ser Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Asp Phe Thr
Leu Lys Ile Ser Arg Val Glu Ala Glu Asp Val Gly Val Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys

Figure 5A

K09A-L-17 light chain full length (SEQ ID NO:20)

```
Asp Ile Val Met Thr Gln Thr Pro Leu Ser Leu Pro Val Thr Pro Gly Glu Pro Ala
Ser Ile Ser Cys Arg Ala Ser Lys Gly Val Ser Thr Ser Gly Tyr Ser Tyr Leu His
Trp Tyr Leu Gln Lys Pro Gly Gln Ser Pro Gln Leu Leu Ile Tyr Leu Ala Ser Tyr
Leu Glu Ser Gly Val Pro Asp Arg Phe Ser Gly Ser Gly Ser Gly Thr Ala Phe Thr
Leu Lys Ile Ser Arg Val Glu Ala Glu Asp Val Gly Leu Tyr Tyr Cys Gln His Ser
Arg Asp Leu Pro Leu Thr Phe Gly Gln Gly Thr Lys Leu Glu Ile Lys Arg Thr Val
Ala Ala Pro Ser Val Phe Ile Phe Pro Pro Ser Asp Glu Gln Leu Lys Ser Gly Thr
Ala Ser Val Val Cys Leu Leu Asn Asn Phe Tyr Pro Arg Glu Ala Lys Val Gln Trp
Lys Val Asp Asn Ala Leu Gln Ser Gly Asn Ser Gln Glu Ser Val Thr Glu Gln Asp
Ser Lys Asp Ser Thr Tyr Ser Leu Ser Ser Thr Leu Thr Leu Ser Lys Ala Asp Tyr
Glu Lys His Lys Val Tyr Ala Cys Glu Val Thr His Gln Gly Leu Ser Ser Pro Val
Thr Lys Ser Phe Asn Arg Gly Glu Cys
```

Figure 5B

Pembrolizumab

Heavy chain (SEQ ID NO:21)

```
QVQLVQSGVE VKKPGASVKV SCKASGYTFT NYYMYWVRQA PGQGLEWMGG  50
INPSNGGTNF NEKFKNRVTL TTDSSTTTAY MELKSLQFDD TAVYYCARRD 100
YRFDMGFDYW GQGTTVTVSS ASTKGPSVFP LAPCSRSTSE STAALGCLVK 150
DYFPEPVTVS WNSGALTSGV HTFPAVLQSS GLYSLSSVVT VPSSSLGTKT 200
YTCNVDHKPS NTKVDKRVES KYGPPCPPCP APEFLGGPSV FLFPPKPKDT 250
LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT 350
LPPSQEEMTK NQVSLTCLVK GFYPSDIAVE WESNGQPENN YKTTPPVLDS 400
DGSFFLYSRL TVDKSRWQEG NVFSCSVMHE ALHNHYTQKS LSLSLGK    447
```

Light chain (SEQ ID NO:22)

```
EIVLTQSPAT LSLSPGERAT LSCRASKGVS TSGYSYLHWY QQKPGQAPRL  50
LIYLASYLES GVPARFSGSG SGTDFTLTIS SLEPEDFAVY YCQHSRDLPL 100
TFGGGTKVEI KRTVAAPSVF IFPPSDEQLK SGTASVVCLL NNFYPREAKV 150
QWKVDNALQS GNSQESVTEQ DSKDSTYSLS STLTLSKADY EKHKVYACEV 200
THQGLSSPVT KSFNRGEC                                   219
```

Figure 6

Nivolumab

Heavy chain (SEQ ID NO:23)

```
QVQLVESGGG VVQPGRSLRL DCKASGITFS NSGMHWVRQA PGKGLEWVAV 50
IWYDGSKRYY ADSVKGRFTI SRDNSKNTLF LQMNSLRAED TAVYYCATND 100
DYWGQGTLVT VSSASTKGPS VFPLAPCSRS TSESTAALGC LVKDYFPEPV 150
TVSWNSGALT SGVHTFPAVL QSSGLYSLSS VVTVPSSSLG TKTYTCNVDH 200
KPSNTKVDKR VESKYGPPCP PCPAPEFLGG PSVFLFPPKP KDTLMISRTP 250
EVTCVVVDVS QEDPEVQFNW YVDGVEVHNA KTKPREEQFN STYRVVSVLT 300
VLHQDWLNGK EYKCKVSNKG LPSSIEKTIS KAKGQPREPQ VYTLPPSQEE 350
MTKNQVSLTC LVKGFYPSDI AVEWESNGQP ENNYKTTPPV LDSDGSFFLY 400
SRLTVDKSRW QEGNVFSCSV MHEALHNHYT QKSLSLSLGK           440
```

Light chain (SEQ ID NO:24)

```
EIVLTQSPAT LSLSPGERAT LSCRASQSVS SYLAWYQQKP GQAPRLLIYD 50
ASNRATGIPA RFSGSGSGTD FTLTISSLEP EDFAVYYCQQ SSNWPRTFGQ 100
GTKVEIKRTV AAPSVFIFPP SDEQLKSGTA SVVCLLNNFY PREAKVQWKV 150
DNALQSGNSQ ESVTEQDSKD STYSLSSTLT LSKADYEKHK VYACEVTHQG 200
LSSPVTKSFN RGEC                                      214
```

Figure 7

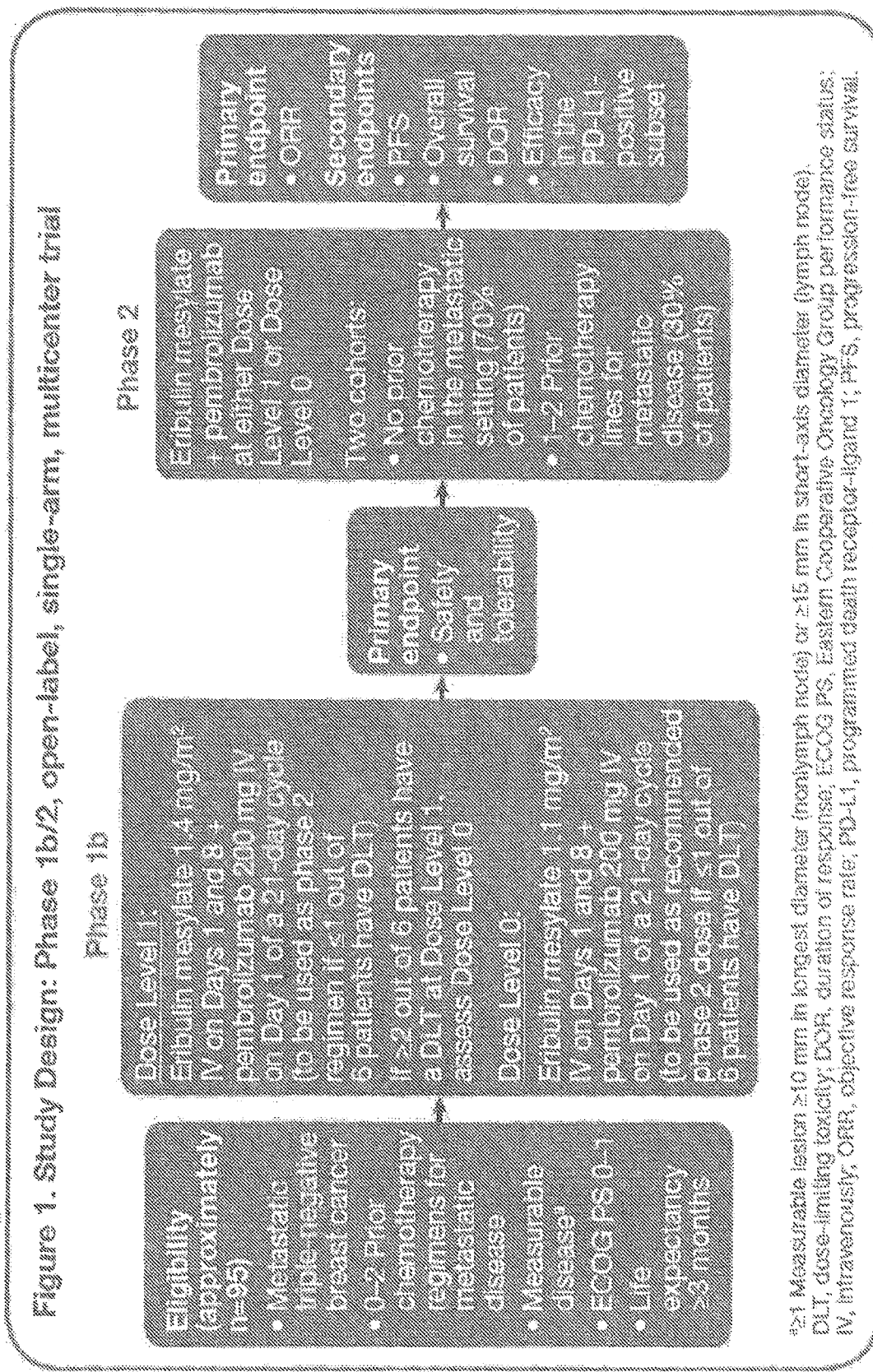

COMBINATION OF A PD-1 ANTAGONIST AND ERIBULIN FOR TREATING CANCER

CROSS REFERENCE TO RELATED APPLICATIONS

This application is the National Stage of International Application No. PCT/US2016/020734, filed Mar. 3, 2016, and claims benefit of U.S. Provisional Application No. 62/128,373 filed on Mar. 4, 2015, and U.S. Provisional Application No. 62/264,068 filed on Dec. 7, 2015.

REFERENCE TO A SEQUENCE LISTING

The instant application contains a sequence listing which has been submitted in ASCII format via EFS-Web and is hereby incorporated by reference in its entirety. Said ASCII copy, created on Dec. 7, 2015, is named 213597_0002_00_US_539597_SL.txt and is 32,003 bytes in size.

FIELD OF THE INVENTION

The present invention relates to combination therapies useful for the treatment of breast cancer. In particular, the invention relates to a combination therapy which comprises an antagonist of a Programmed Death 1 protein (PD-1) and eribulin or a pharmaceutically acceptable salt thereof.

BACKGROUND OF THE INVENTION

PD-1 is recognized as an important player in immune regulation and the maintenance of peripheral tolerance. PD-1 is moderately expressed on naive T, B, and NKT cells and up-regulated by T/B cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and cancer cell evasion of immune surveillance, thereby contributing to an impaired immune response against the tumor.

Several monoclonal antibodies that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

SUMMARY OF THE INVENTION

In one embodiment, the invention provides a method for treating breast cancer or melanoma in an individual comprising administering to the individual a combination therapy which comprises a PD-1 antagonist and eribulin or a pharmaceutically acceptable salt thereof (e.g., eribulin mesylate).

In another embodiment, the invention provides a medicament comprising a PD-1 antagonist for use in combination with eribulin or a pharmaceutically acceptable salt thereof (e.g., eribulin mesylate) for treating breast cancer or melanoma.

In yet another embodiment, the invention provides a medicament comprising eribulin or a pharmaceutically acceptable salt thereof (e.g., eribulin mesylate) for use in combination with a PD-1 antagonist for treating breast cancer or melanoma.

Other embodiments provide use of a PD-1 antagonist in the manufacture of a medicament for treating breast cancer or melanoma in an individual when administered in combination with eribulin or a pharmaceutically acceptable salt thereof (e.g., eribulin mesylate) and use of eribulin or a pharmaceutically acceptable salt thereof (e.g., eribulin mesylate) in the manufacture of a medicament for treating breast cancer or melanoma in an individual when administered in combination with a PD-1 antagonist.

In a still further embodiment, the invention provides use of a PD-1 antagonist and eribulin or a pharmaceutically acceptable salt thereof (e.g., eribulin mesylate) in the manufacture of medicaments for treating breast cancer or melanoma in an individual. In some embodiments, the medicaments comprise a kit, and the kit can also comprise a package insert comprising instructions for using the PD-1 antagonist in combination with eribulin or a pharmaceutically acceptable salt thereof (e.g., eribulin mesylate) to treat breast cancer or melanoma in an individual.

In all of the above treatment methods, medicaments, and uses, the PD-1 antagonist inhibits the binding of PD-L1 to PD-1, and preferably also inhibit the binding of PD-L2 to PD-1. In some embodiments of the above treatment methods, medicaments and uses, the PD-1 antagonist is a monoclonal antibody, or an antigen binding fragment thereof, which specifically binds to PD-1 or to PD-L1 and blocks the binding of PD-L1 to PD-1. In one embodiment, the PD-1 antagonist is an anti-PD-1 antibody which comprises a heavy chain and a light chain, and wherein the heavy and light chains comprise the amino acid sequences shown in FIG. 6 (SEQ ID NO: 21 and SEQ ID NO: 22).

In all of the above embodiments of the treatment methods, medicaments, and uses herein, the eribulin is optionally eribulin mesylate.

In some embodiments of the above treatment methods, medicaments, and uses, the individual is a human, and the breast cancer is metastatic breast cancer and/or triple negative breast cancer.

Also, in some embodiments of any of the above treatment methods, medicaments, and uses, the breast cancer or melanoma tests positive for the expression of one or both of PD-L1 and PD-L2. In still other embodiments, the breast cancer or melanoma has elevated PD-L1 expression.

In one embodiment of the above treatment methods, medicaments, and uses, the individual is a human and the cancer is breast cancer (e.g., metastatic and/or triple negative breast cancer) that tests positive for human PD-L1.

In another embodiment of the above treatment methods, medicaments, and uses, the breast cancer is previously treated with 0, 1, or 2 lines of chemotherapy in the metastatic setting.

BRIEF DESCRIPTION OF THE DRAWINGS

FIG. 1 shows amino acid sequences of the light chain and heavy chain CDRs for an exemplary anti-PD-1 monoclonal antibody useful in the present invention (SEQ ID NOs: 1-6).

FIG. 2 shows amino acid sequences of the light chain and heavy chain CDRs for another exemplary anti-PD-monoclonal antibody useful in the present invention (SEQ ID NOs: 7-12).

FIG. 3 shows amino acid sequences of the heavy chain variable region and full length heavy chain for an exemplary anti-PD-1 monoclonal antibody useful in the present invention (SEQ ID NO: 13 and SEQ ID NO: 14).

FIG. 4 shows amino acid sequences of alternative light chain variable regions for an exemplary anti-PD-1 monoclonal antibody useful in the present invention (SEQ ID NOs: 15-17).

FIG. 5 shows amino acid sequences of alternative light chains for an exemplary anti-PD-1 monoclonal antibody useful in the present invention, with FIG. 5A showing the amino acid sequences for the K09A-L-11 and K09A-L-16 light chains (SEQ ID NOs: 18 and 19, respectively) and FIG. 5B showing the amino acid sequence for the K09A-L-17 light chain (SEQ ID NO: 20).

FIG. 6 shows amino acid sequences of the heavy and light chains for pembrolizumab (SEQ ID NOs: 21 and 22, respectively).

FIG. 7 shows amino acid sequences of the heavy and light chains for nivolumab (SEQ ID NOs: 23 and 24, respectively).

FIG. 8 shows a study design of a phase 1b/2, open label, single-arm, multicenter trial.

DETAILED DESCRIPTION

I. Abbreviations

Throughout the detailed description and examples of the invention the following abbreviations will be used:
AE Adverse Event
ANC Absolute Neutrophil Count
BOR Best overall response
CDR Complementarity determining region
CHO Chinese hamster ovary
CR Complete Response
DFS Disease free survival
DLT Dose-Limiting Toxicity
DOR Duration of Response
FFPE Formalin-fixed, paraffin-embedded
FR Framework region
IHC Immunohistochemistry or immunohistochemical
irRC Immune related response criteria
mTNBC metastatic triple negative breast cancer
NCBI National Center for Biotechnology Information
OR Overall response
OS Overall survival
PD Progressive Disease
PD-1 Programmed Death 1
PD-L1 Programmed Cell Death 1 Ligand 1
PD-L2 Programmed Cell Death 1 Ligand 2
PFS Progression free survival
PP Predictive Probability
PR Partial Response
Q2W One dose every two weeks
Q3W One dose every three weeks
RECIST Response Evaluation Criteria in Solid Tumors
SD Stable Disease
VH Immunoglobulin heavy chain variable region
VK Immunoglobulin kappa light chain variable region

I. Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the dosage of a PD-1 antagonist (or eribulin or a pharmaceutically acceptable salt thereof (e.g., eribulin mesylate)), or the length of treatment time with a PD-1 antagonist (or eribulin or a pharmaceutically acceptable salt thereof (e.g., eribulin mesylate))) means that the parameter may vary by as much as 10% above or below the stated numerical value for that parameter.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, and rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full-length monoclonal antibodies), polyclonal antibodies, multispecific antibodies (e.g., bispecific antibodies), humanized and primatized antibodies, fully human antibodies, chimeric antibodies, and camelized single domain antibodies. "Parental antibodies" are antibodies obtained by exposure of an immune system to an antigen prior to modification of the antibodies for an intended use, such as humanization of a parental antibody generated in a mouse for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Human light chains can be classified as kappa and lambda light chains. Furthermore, human heavy chains can be classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of *Sequences of Proteins of Immunological Interest*, Kabat, et al.; National Institutes of Health, Bethesda, Md.; $5^{th}$ ed.; NIH Publ. No. 91-3242 (1991); Kabat (1978) *Adv. Prot. Chem.* 32: 1-75; Kabat, et al., (1977) *J. Biol. Chem.* 252: 6609-6616; Chothia, et al., (1987) *J. Mol. Biol.* 196: 901-917 or Chothia, et al., (1989) *Nature* 342: 878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2, and CDRL3 in the light chain variable domain and CDRH1, CDRH2, and CDRH3 in the heavy chain variable domain). See Kabat et al. (1991) SEQUENCES OF PROTEINS OF IMMUNOLOGICAL INTEREST, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of a mature human PD-1 or human PD-L1 molecule, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will generally comprise the same CDR sequences of the parental rodent antibodies, although certain amino acid substitutions may be included to increase affinity, increase stability of the humanized antibody, or for other reasons.

An "anti-tumor response" when referring to a cancer patient treated with a therapeutic agent, such as a PD-1 antagonist, means at least one positive therapeutic effect, such as a reduced number of cancer cells, a reduced tumor size, a reduced rate of cancer cell infiltration into peripheral organs, a reduced rate of tumor metastasis or tumor growth, or progression free survival. Positive therapeutic effects in cancer can be measured in a number of ways (See e.g., W. A. Weber, J. *Null. Med.* 50: 1S-10S (2009); Eisenhauer et al., supra). In some embodiments, an anti-tumor response to a PD-1 antagonist is assessed using RECIST 1.1 criteria, bidimentional irRC, or unidimensional irRC. In some embodiments, an anti-tumor response is any of SD, PR, CR, PFS, and DFS.

"Bidimensional irRC" refers to the set of criteria described in Wolchok J D, et al. Guidelines for the evaluation of immune therapy activity in solid tumors: immune-related response criteria. *Clin Cancer Res.* 2009; 15(23): 7412-7420. These criteria utilize bidimensional tumor measurements of target lesions, which are obtained by multiplying the longest diameter and the longest perpendicular diameter (cm$^2$) of each lesion.

"Biotherapeutic agent" means a biological molecule, such as an antibody or fusion protein, that blocks ligand/receptor signaling in any biological pathway that supports tumor maintenance and/or growth or suppresses the anti-tumor immune response.

The terms "cancer," "cancerous," or "malignant" refer to or describe the physiological condition in mammals that is typically characterized by unregulated cell growth. Examples of cancer include breast cancer (e.g., metastatic and/or triple negative breast cancer) and melanoma. Particularly preferred breast cancers or melanoma that may be treated in accordance with the present invention include those characterized by elevated expression of one or both of PD-L1 and PD-L2 in tested tissue samples.

"CDR" or "CDRs" as used herein means complementarity determining region(s) in an immunoglobulin variable region, defined using the Kabat numbering system, unless otherwise indicated.

"Chemotherapeutic agent" is a chemical compound useful in the treatment of cancer. Classes of chemotherapeutic agents include, but are not limited to: alkylating agents, antimetabolites, kinase inhibitors, spindle poison plant alkaloids, cytoxic/antitumor antibiotics, topoisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists, anti-androgens, aromatase inhibitors, epidermal growth factor receptor (EGFR) inhibitors, vascular engothelial growth factor (VEGF) inhibitors, anti-sense oligonucleotides that that inhibit expression of genes implicated in abnormal cell proliferation or tumor growth. Chemotherapeutic agents useful in the treatment methods of the present invention include cytostatic and/or cytotoxic agents.

"Chothia" as used herein means an antibody numbering system described in Al-Lazikani et al., *JMB* 273:927-948 (1997).

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a PD-1 antagonist that consists essentially of a recited amino acid sequence may also include one or more amino acids, including substitutions of one or more amino acid residues, which do not materially affect the properties of the binding compound.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |

TABLE 1-continued

Exemplary Conservative Amino Acid Substitutions

| Original residue | Conservative substitution |
|---|---|
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Diagnostic anti-PD-L monoclonal antibody" means a mAb which specifically binds to the mature form of the designated PD-L (PD-L1 or PDL2) that is expressed on the surface of certain mammalian cells. A mature PD-L lacks the presecretory leader sequence, also referred to as leader peptide. The terms "PD-L" and "mature PD-L" are used interchangeably herein, and mean the same molecule unless otherwise indicated or readily apparent from the context.

As used herein, a diagnostic anti-human PD-L1 mAb or an anti-hPD-L1 mAb refers to a monoclonal antibody that specifically binds to mature human PD-L1. A mature human PD-L1 molecule consists of amino acids 19-290 of the following sequence:

(SEQ ID NO: 25)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

Specific examples of diagnostic anti-human PD-L1 mAbs useful as diagnostic mAbs for immunohistochemistry (IHC) detection of PD-L1 expression in formalin-fixed, paraffin-embedded (FFPE) tumor tissue sections are antibody 20C3 and antibody 22C3, which are described in the copending international patent application PCT/US13/075932, filed 18 Dec. 2013 and published as WO2014/100079 on 26 Jun. 2014. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P.R. China; Catalog number 10084-R015).

"Dose-limiting toxicity" or "DLT" as used herein means toxicities occurring during the DLT assessment window and considered to be related to pembrolizumab and/or eribulin. Toxicities can include hematologic toxicities (e.g., any Grade 4 thrombocytopenia or neutropenia lasting >7 days) and/or non-hematologic toxicities (e.g., episcleritis, uveitis, or iritis of Grade 2 or higher, Grade 4 toxicity, any Grade 3 toxicity excluding nausea, vomiting, or diarrhea that is controlled by medical intervention within 72 hrs.).

"Duration of Response" is defined as the time from the date that a confirmed objective response is first documented to the date of PD or death due to any cause for those subjects with a confirmed PR or CR.

"Framework region" or "FR" as used herein means the immunoglobulin variable regions excluding the CDR regions.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a polynucleotide alignment algorithm, BLAST®, which is a registered trademark of the National Library of Medicine, wherein the parameters of the algorithm are selected to give the largest match between the respective sequences over the entire length of the respective reference sequences.

The following references relate to BLAST® algorithms often used for sequence analysis: BLAST ALGORITHMS: Altschul, S. F., et al., (1990) *J. Mol. Biol.* 215: 403-410; Gish, W., et al., (1993) *Nature Genet.* 3: 266-272; Madden, T. L., et al., (1996) *Meth. Enzymol.* 266: 131-141; Altschul, S. F., et al., (1997) *Nucleic Acids Res.* 25: 3389-3402; Zhang, J., et al., (1997) *Genome Res.* 7: 649-656; Wootton, J. C., et al., (1993) *Comput. Chem.* 17: 149-163; Hancock, J. M. et al., (1994) *Comput. Appl. Biosci.* 10: 67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) *J. Mol. Biol.* 219: 555-565; States, D. J., et al., (1991) *Methods* 3: 66-70; Henikoff, S., et al., (1992) *Proc. Natl. Acad Sci. USA* 89: 10915-10919; Altschul, S. F., et al., (1993)*J. Mol. Evol.* 36: 290-300; ALIGNMENT STATISTICS: Karlin, S., et al., (1990) *Proc. Natl. Acad. Sci. USA* 87: 2264-2268; Karlin, S., et al., (1993) *Proc. Natl. Acad. Sci. USA* 90: 5873-5877; Dembo, A., et al., (1994) *Ann. Prob.* 22: 2022-2039; and Altschul, S. F. "Evaluating the statistical significance of multiple distinct local alignments." IN THEORETICAL AND COMPUTATIONAL METHODS IN GENOME RESEARCH (S. Suhai, ed.), (1997) pp. 1-14, Plenum, N.Y. "Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" and "purified" are not intended to refer to a complete absence of such material or to an absence of water, buffers, or salts, unless they are present in amounts that substantially interfere with experimental or therapeutic use of the binding compound as described herein.

"Isolated antibody" and "isolated antibody fragment" refers to the purification status and in such context means the named molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116: 731.

"Non-responsder patient" when referring to a specific anti-tumor response to treatment with a PD-1 antagonist, means the patient did not exhibit the anti-tumor response to the administered PD-1 antagonist treatment.

"Patient" refers to any single human subject for which therapy is desired or that is participating in a clinical trial, epidemiological study or used as a control.

"PD-1 antagonist" means any chemical compound or biological molecule that blocks binding of PD-L1 expressed on a cancer cell to PD-1 expressed on an immune cell (T cell, B cell, or natural killer T (NKT) cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274, and B7-H for PD-L1; and PDCD1L2, PDL2, B7-DC, Btdc and CD273 for PD-L2. In any of the various aspects and embodiments of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the various aspects and embodiments of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment methods, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in the treatment methods, medicaments and uses of the present invention include: pembrolizumab (also known as MK-3475), a humanized IgG4 mAb with the structure described in *WHO Drug Information*, Vol. 27, No. 2, pages 161-162 (2013) and which comprises the heavy and light chain amino acid sequences shown in FIG. 6, nivolumab (BMS-936558), a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by MedImmune.

Examples of mAbs that bind to human PD-L1, and useful in any of the various aspects and embodiments of the present invention, are described in WO2013/019906, WO2010/077634 A1 and U.S. Pat. No. 8,383,796. Specific anti-human PD-L1 mAbs useful as the PD-1 antagonist in the various aspects and embodiments of the present invention include MPDL3280A, BMS-936559, MEDI4736, MSB0010718C and an antibody which comprises the heavy chain and light chain variable regions of SEQ ID NO: 24 and SEQ ID NO: 21, respectively, of WO2013/019906.

Other PD-1 antagonists useful in any of the various aspects and embodiments of the present invention include an immunoadhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment methods, medicaments and uses of the present invention include AMP-224 (also known as B7-DCIg), which is a PD-L2-FC fusion protein and binds to human PD-1.

In some preferred embodiments of the treatment methods, medicaments and uses of the present invention, the PD-1 antagonist is a monoclonal antibody, or antigen binding fragment thereof, which comprises: (a) light chain CDRs SEQ ID NOs: 1, 2 and 3 and heavy chain CDRs SEQ ID NOs: 4, 5 and 6; or (b) light chain CDRs SEQ ID NOs: 7, 8 and 9 and heavy chain CDRs SEQ ID NOs: 10, 11 and 12.

In other preferred embodiments of the treatment methods, medicaments and uses of the present invention, the PD-1 antagonist is a monoclonal antibody, or antigen binding fragment thereof, which specifically binds to human PD-1 and comprises (a) a heavy chain variable region comprising SEQ ID NO: 13 or a variant thereof, and (b) a light chain variable region comprising an amino acid sequence selected from the group consisting of SEQ ID NO: 15 or a variant thereof; SEQ ID NO: 16 or a variant thereof; and SEQ ID NO: 17 or a variant thereof. A variant of a heavy chain variable region sequence is identical to the reference sequence except having up to 17 conservative amino acid substitutions in the framework region (i.e., outside of the CDRs), and preferably has less than ten, nine, eight, seven, six, five, four, three, two, or one conservative amino acid substitutions in the framework region. A variant of a light chain variable region sequence is identical to the reference sequence except having up to five conservative amino acid substitutions in the framework region (i.e., outside of the CDRs), and preferably has less than four, three, two or one conservative amino acid substitution in the framework region.

In another preferred embodiment of the treatment methods, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO: 18, SEQ ID NO: 19, or SEQ ID NO: 20.

In yet another preferred embodiment of the treatment methods, medicaments and uses of the present invention, the PD-1 antagonist is a monoclonal antibody which specifically binds to human PD-1 and comprises (a) a heavy chain comprising SEQ ID NO: 14 and (b) a light chain comprising SEQ ID NO: 18.

Table 2 below provides a list of the amino acid sequences of exemplary anti-PD-1 mAbs for use in the treatment methods, medicaments, and uses of the present invention, and the sequences are shown in FIGS. 1-5.

TABLE 2

| EXEMPLARY ANTI-HUMAN PD-1 MONOCLONAL ANTIBODIES | |
|---|---|
| A. Comprises light and heavy chain CDRs of hPD-1.08A in WO2008/156712 | |
| CDRL1 | SEQ ID NO: 1 |
| CDRL2 | SEQ ID NO: 2 |
| CDRL3 | SEQ ID NO: 3 |
| CDRH1 | SEQ ID NO: 4 |
| CDRH2 | SEQ ID NO: 5 |
| CDRH3 | SEQ ID NO: 6 |
| B. Comprises light and heavy chain CDRs of hPD-1.09A in WO2008/156712 | |
| CDRL1 | SEQ ID NO: 7 |
| CDRL2 | SEQ ID NO: 8 |
| CDRL3 | SEQ ID NO: 9 |
| CDRH1 | SEQ ID NO: 10 |
| CDRH2 | SEQ ID NO: 11 |
| CDRH3 | SEQ ID NO: 12 |
| C. Comprises the mature h109A heavy chain variable region and one of the mature K09A light chain variable regions in WO2008/156712 | |
| Heavy chain VR | SEQ ID NO: 13 |
| Light chain VR | SEQ ID NO: 15, SEQ ID NO: 16, or SEQ ID NO: 17 |
| D. Comprises the mature 409 heavy chain and one of the mature K09A light chains in WO2008/156712 | |
| Heavy chain | SEQ ID NO: 14 |
| Light chain | SEQ ID NO: 18, SEQ ID NO: 19, or SEQ ID NO: 20 |

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by positron emission tomography (PET) imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

Several approaches have been described for quantifying PD-L1 protein expression in IHC assays of tumor tissue sections. See, e.g., Thompson, R. H., et al., *PNAS* 101 (49): 17174-17179 (2004); Thompson, R. H. et al., *Cancer Res.* 66: 3381-3385 (2006); Gadiot, J., et al., *Cancer* 117: 2192-2201 (2011); Taube, J. M. et al., *Sci Transl Med* 4: 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

A "pembrolizumab biosimilar" means a biological product manufactured by an entity other than Merck Sharpe & Dohme and which is approved by a regulatory agency in any country for marketing as a pembrolizumab biosimilar. In an embodiment, a pembrolizumab biosimilar comprises a pembrolizumab variant as the drug substance. In an embodiment, a pembrolizumab biosimilar has the same amino acid sequence as pembrolizumab.

As used herein, a "pembrolizumab variant" means a monoclonal antibody which comprises heavy chain and light chain sequences that are identical to those in pembrolizumab, except for having three, two, or one conservative amino acid substitutions at positions that are located outside of the light chain CDRs and six, five, four, three, two, or one conservative amino acid substitutions that are located outside of the heavy chain CDRs, e.g., the variant positions are located in the FR regions or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

"RECIST 1.1 Response Criteria" as used herein means the definitions set forth in Eisenhauer et al., E. A. et al., *Eur. J. Cancer* 45: 228-247 (2009) for target lesions or nontarget lesions, as appropriate based on the context in which response is being measured.

"Responsder patient" when referring to a specific anti-tumor response to treatment with a combination therapy described herein, means the patient exhibited the anti-tumor response.

"Sample" when referring to a tumor or any other biological material referenced herein, means a sample that has been removed from the subject; thus, none of the testing methods described herein are performed in or on the subject.

"Sustained response" means a sustained therapeutic effect after cessation of treatment with a therapeutic agent, or a combination therapy described herein. In some embodiments, the sustained response has a duration that is at least the same as the treatment duration, or at least 1.5, 2.0, 2.5, or 3 times longer than the treatment duration.

"Tissue Section" refers to's single part or piece of a tissue sample, e.g., a thin slice of tissue cut from a sample of a normal tissue or of a tumor.

"Treat" or "treating" a cancer as used herein means to administer a PD-1 antagonist and eribulin or a pharmaceutically acceptable salt thereof (e.g., eribulin mesylate), or another therapeutic agent to a subject having a cancer, or diagnosed with a cancer, to achieve at least one positive therapeutic effect, such as for example, reduced number of cancer cells, reduced tumor size or tumor burden, reduced rate of cancer cell infiltration into peripheral organs, or reduced rate of tumor metastasis or tumor growth. Positive therapeutic effects in cancer can be measured in a number of ways (See, W. A. Weber, J. *Null. Med.* 50: 1S-10S (2009); Eisenhauer et al., supra). In some preferred embodiments, response to a PD-1 antagonist is assessed using RECIST 1.1 criteria or irRC. In some embodiments, the treatment achieved by a therapeutically effective amount is any of PR, CR, PFS, DFS, OR, or overall survival (OS). In some preferred embodiments, a gene signature biomarker of the invention predicts whether a subject with a solid tumor is likely to achieve a PR or a CR. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment methods, medicaments and uses of the present invention may not be effective in achieving a positive therapeutic effect in every subject, it should do so in a statistically significant number of subjects as determined by any statistical test known in the art such as the Student's t-test, the $\chi^2$-test, the U-test according to Mann and Whitney, the Kruskal-Wallis test (H-test), Jonckheere-Terpstra-test, and the Wilcoxon-test.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load," refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

"Unidimensional irRC refers to the set of criteria described in Nishino M, Giobbie-Hurder A, Gargano M, Suda M, Ramaiya N H, Hodi F S. "Developing a Common Language for Tumor Response to Immunotherapy: Immune-related Response Criteria using Unidimensional measurements." *Clin Cancer Res.* 2013; 19(14): 3936-3943). These criteria utilize the longest diameter (cm) of each lesion.

"Variable regions" or "V region" as used herein means the segment of IgG chains for example which is variable in sequence between different antibodies. It extends to Kabat residue 109 in the light chain and 113 in the heavy chain.

"Eribulin" is a synthetic analog of halichondrin B. Eribulin is also known as ER-086526, and has been assigned CAS number 253128-41-5 and US NCI designation number NSC-707389. The mesylate salt of eribulin (eribulin mesylate, which is marketed under the trade name HALAVEN® and is also known as E7389) is approved for the treatment of patients with breast cancer who have previously received at least two chemotherapeutic regimens for the treatment of metastatic disease that should have included an anthracycline and a taxane in either the adjuvant or metastatic setting.

The chemical name for eribulin mesylate is 11,15:18,21:24,28-triepoxy-7,9-ethano-12,15-methano-9H,15H-furo[3,2-i]furo[2',3':5,6]pyrano[4,3-b][1,4]dioxacyclopentacosin-5(4H)-one, 2-[(2S)-3-amino-2-hydroxypropyl]hexacosahydro-3-methoxy-26-methyl-20,27-bis(methylene)-, (2R,3R,3aS,7R,8aS,9S,10aR,11S,12R,13aR,13bS,15S,18S,21S,24S,26R,28R,29aS)-methanesulfonate (salt), and it can be depicted as follows:

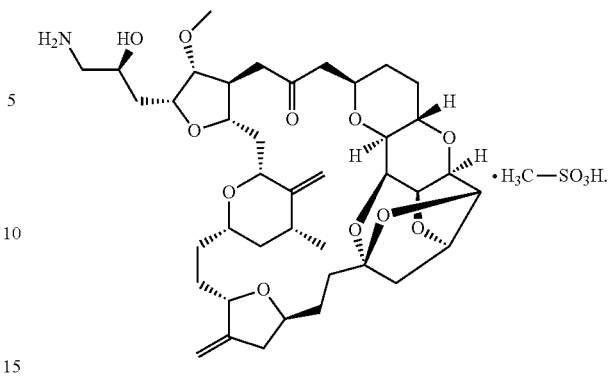

Methods for synthesizing eribulin are described, for example, in U.S. Pat. Nos. 6,214,865; 7,982,060; 8,350,067; and 8,093,410, each of which is incorporated herein by reference. Eribulin mesylate is available commercially and is marketed as HALAVEN®.

As noted above, eribulin can optionally be used in the present invention in salt forms. There are no particular limitations as to the salt used, whether inorganic acid salt or organic acid salt. For example, the salt can be selected from mesylic acid salt (e.g., eribulin mesylate), hydrochloric acid salt, sulfuric acid salt, citrate, hydrobromic acid salt, hydroiodine acid salt, nitric acid salt, bisulfate, phosphoric acid salt, super phosphoric acid salt, isonicotinic acid salt, acetic acid salt, lactic acid salt, salicic acid salt, tartaric acid salt, pantotenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate), and so on. Moreover, it is acceptable to use salt of aluminum, calcium, lithium, magnesium, sodium, zinc, and diethanolamine.

Eribulin is typically provided in liquid form, for intravenous administration

I. Methods, Uses and Medicaments

In one aspect of the invention, the invention provides a method for treating breast cancer or melanoma in an individual comprising administering to the individual a combination therapy which comprises a PD-1 antagonist and eribulin or a pharmaceutically acceptable salt thereof (e.g., eribulin mesylate).

The combination therapy may also comprise one or more additional therapeutic agents. The additional therapeutic agent may be, e.g., a chemotherapeutic other than eribulin or a pharmaceutically acceptable salt thereof (e.g., eribulin mesylate), a biotherapeutic agent, an immunogenic agent (for example, attenuated cancerous cells, tumor antigens, antigen presenting cells such as dendritic cells pulsed with tumor derived antigen or nucleic acids, immune stimulating cytokines (for example, IL-2, IFNα2, GM-CSF), and cells transfected with genes encoding immune stimulating cytokines such as but not limited to GM-CSF).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine;

acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor 9-nitrocamptothecin (RFS 2000); difluoromethylornithine (DMFO); retinoids such as retinoic acid; capecitabine; and pharmaceutically acceptable salts, acids or derivatives of any of the above. Also included are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, and goserelin; and pharmaceutically acceptable salts, acids or derivatives of any of the above.

Each therapeutic agent in a combination therapy of the invention may be administered either alone or in a medicament (also referred to herein as a pharmaceutical composition) which comprises one or more therapeutic agents and one or more pharmaceutically acceptable carriers, excipients and diluents, according to standard pharmaceutical practice.

Each therapeutic agent in a combination therapy of the invention may be administered simultaneously (i.e., in the same medicament), concurrently (i.e., in separate medicaments administered one right after the other in any order) or sequentially in any order. Sequential administration is particularly useful when the therapeutic agents in the combination therapy are in different dosage forms (one agent is a tablet or capsule and another agent is a sterile liquid) and/or are administered on different dosing schedules, e.g., a chemotherapeutic that is administered at least daily and a biotherapeutic that is administered less frequently, such as once weekly, once every two weeks, or once every three weeks.

In some embodiments, the eribulin or pharmaceutically acceptable salt thereof (e.g., eribulin mesylate) is administered before administration of the PD-1 antagonist, while in other embodiments, the eribulin or pharmaceutically acceptable salt thereof (e.g., eribulin mesylate) is administered after administration of the PD-1 antagonist.

In some embodiments, at least one of the therapeutic agents in the combination therapy is administered using the same dosage regimen (dose, frequency, and duration of treatment) that is typically employed when the agent is used as monotherapy for treating the same cancer. In other coembodiments, the patient receives a lower total amount of at least one of the therapeutic agents in the combination therapy than when the agent is used as monotherapy, e.g., smaller doses, less frequent doses, and/or shorter treatment duration.

Each small molecule therapeutic agent in a combination therapy of the invention can be administered orally or parenterally, including the intravenous, intramuscular, intraperitoneal, subcutaneous, rectal, topical, and transdermal routes of administration.

A combination therapy of the invention may be used prior to or following surgery to remove a tumor and may be used prior to, during or after radiation therapy.

In some embodiments, a combination therapy of the invention is administered to a patient who has not been previously treated with a biotherapeutic or chemotherapeutic agent, i.e., is treatment-naïve. In other embodiments, the combination therapy is administered to a patient who failed to achieve a sustained response after prior therapy with a biotherapeutic or chemotherapeutic agent, i.e., is treatment-experienced.

A combination therapy of the invention is typically used to treat a tumor that is large enough to be found by palpation or by imaging techniques well known in the art, such as MRI, ultrasound, or computerized axial tomography (CAT) scan.

A combination therapy of the invention is preferably administered to a human patient who has breast cancer or melanoma that tests positive for PD-L1 expression. In some preferred embodiments, PD-L1 expression is detected using a diagnostic anti-human PD-L1 antibody, or antigen binding fragment thereof, in an IHC assay on an FFPE or frozen tissue section of a tumor sample removed from the patient. Typically, the patient's physician would order a diagnostic test to determine PD-L1 expression in a tumor tissue sample removed from the patient prior to initiation of treatment with the PD-1 antagonist and eribulin or a pharmaceutically acceptable salt thereof (e.g., eribulin mesylate), but it is envisioned that the physician could order the first or subsequent diagnostic tests at any time after initiation of treatment, such as for example after completion of a treatment cycle.

Selecting a dosage regimen (also referred to herein as an administration regimen) for a combination therapy of the invention depends on several factors, including the serum or tissue turnover rate of the entity, the level of symptoms, the immunogenicity of the entity, and the accessibility of the target cells, tissue or organ in the individual being treated. Preferably, a dosage regimen maximizes the amount of each therapeutic agent delivered to the patient consistent with an acceptable level of side effects. Accordingly, the dose amount and dosing frequency of each biotherapeutic and chemotherapeutic agent in the combination depends in part on the particular therapeutic agent, the severity of the cancer being treated, and patient characteristics. Guidance in selecting appropriate doses of antibodies, cytokines, and small molecules are available. See, e.g., Wawrzynczak (1996) *Antibody Therapy*, Bios Scientific Pub. Ltd., Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med* 348: 601-608; Milgrom et al. (1999) *New Engl. J. Med*. 341: 1966-1973; Slamon et al. (2001) *New Engl. J. Med*. 344: 783-792; Beniaminovitz et al. (2000) *New Engl. J. Med*. 342: 613-619; Ghosh et al. (2003) *New Engl. J. Med* 348: 24-32; Lipsky et al. (2000) *New Engl. J. Med* 343: 1594-1602; PHYSICIANS' DESK REFERENCE 2003 (Physicians' Desk Reference, 57th Ed.); Medical Economics Company; ISBN: 1563634457; 57th edition (November 2002). Determination of the appropriate dosage regimen may be made by the clinician, e.g., using parameters or factors known or suspected in the art to affect treatment or predicted to affect treatment, and will depend, for example, the patient's clinical history (e.g., previous therapy), the type and stage of the cancer to be treated and biomarkers of response to one or more of the therapeutic agents in the combination therapy.

Biotherapeutic agents in a combination therapy of the invention may be administered by continuous infusion, or by doses at intervals of, e.g., daily, every other day, three times per week, or one time each week, two weeks, three weeks, monthly, bimonthly, etc. A total weekly dose is generally at least 0.05 μg/kg, 0.2 μg/kg, 0.5 μg/kg, 1 μg/kg, 10 μg/kg, 100 μg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med* 349: 427-434; Herold et al. (2002) *New Engl. J. Med*. 346: 1692-1698; Liu et al. (1999) *J. Neurol. Neurosurg. Psych*. 67: 451-456; Portielji et al. (2003) *Cancer Immunol. Immunother.* 52: 133-144.

In some embodiments that employ an anti-human PD-1 mAb as the PD-1 antagonist in the combination therapy, the dosing regimen will comprise administering the anti-human PD-1 mAb at a dose of 1, 2, 3, 5, or 10 mg/kg at intervals of about 14 days (±2 days) or about 21 days (±2 days) or about 30 days (±2 days) throughout the course of treatment.

In other embodiments that employ an anti-human PD-1 mAb as the PD-1 antagonist in the combination therapy, the dosing regimen will comprise administering the anti-human PD-1 mAb at a dose of from about 0.005 mg/kg to about 10 mg/kg, with intra-patient dose escalation. In other escalating dose embodiments, the interval between doses will be progressively shortened, e.g., about 30 days (±2 days) between the first and second dose, about 14 days (±2 days) between the second and third doses. In certain embodiments, the dosing interval will be about 14 days (±2 days), for doses subsequent to the second dose.

In certain embodiments, a subject will be administered an intravenous (IV) infusion of a medicament comprising any of the PD-1 antagonists described herein.

In one preferred embodiment of the invention, the PD-1 antagonist in the combination therapy is prembrolizumab, which is administered intravenously at a dose selected from the group consisting of: 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, and 10 mg Q3W.

In another preferred embodiment of the invention, the PD-1 antagonist in the combination therapy is pembrolizumab, which is administered in a liquid medicament at a dose selected from the group consisting of 1 mg/kg Q2W, 2 mg/kg Q2W, 3 mg/kg Q2W, 5 mg/kg Q2W, 10 mg Q2W, 1 mg/kg Q3W, 2 mg/kg Q3W, 3 mg/kg Q3W, 5 mg/kg Q3W, 10 mg Q3W, and flat-dose equivalents of any of these doses, i.e., such as 200 mg Q3W. In some embodiments, pembrolizumab is administered as a liquid medicament which comprises 25 mg/ml pembrolizumab, 7% (w/v) sucrose, 0.02% (w/v) polysorbate 80 in 10 mM histidine buffer pH 5.5, and the selected dose of the medicament is administered by IV infusion over a time period of about 30 minutes.

The optimal dose for pembrolizumab in combination with eribulin or a pharmaceutically acceptable salt thereof may be identified by dose escalation of one or both of these agents. In one embodiment, eribulin or a pharmaceutically acceptable salt thereof (e.g., eribulin mesylate) is administered intravenously over about 2-5 minutes at 1.4 mg/m$^2$ on days 1 and 8 of a 21-day cycle, and pembrolizumab is administered intravenously over about 30 minutes at 200 mg on day 1 of a 21-day cycle.

FIG. 8 shows a study design of a phase 1b/2, open label, single-arm, multicenter trial. A total of approximately 95 adult patients can be enrolled, including twelve in the phase 1b and 83 in the phase 2 part of the trial, with 80 patients estimated to be evaluable for the primary analysis. The dose-limiting toxicity (DLT) of the combination regimen of pembrolizumab and eribulin may be determined in the phase 1b part of the trial, which may include a single initial run-in cohort in which at least six patients (up to a maximum of twelve) may receive eribulin mesylate 1.4 mg/m2 (equivalent to 1.23 mg/m2 eribulin [expressed as free base]) administered intravenously (IV) on days 1 and 8 and pembrolizumab 200 mg IV on day 1 of a 21-day cycle (Dose Level 1). If one or fewer out of six patients has a DLT at Dose Level 1, this regimen may be selected for use in the phase 2 portion of the trial. Otherwise, the eribulin dose may be lowered to 1.1 mg/m$^2$ on Days 1 and 8 of the 21-day cycle (Dose Level 0). If one or fewer out of six patients experiences a DLT, the phase 2 portion of the trial may proceed using Dose Level 0 as shown in FIG. 8. In the phase 2 part of the trial, patients may be enrolled in two cohorts according to receipt of prior chemotherapy in the metastatic setting (none vs. 1-2 prior lines). Patients may undergo treatment as long as clinical benefit is demonstrated or until intercurrent illness, unacceptable toxicity, disease progression, withdrawal of consent, or death.

In another embodiment, eribulin or a pharmaceutically acceptable salt thereof (e.g., eribulin mesylate) is administered at 1.4 mg/m² on days 1 and 15 of a 28-day cycle and pembrolizumab is administered intravenously at 200 mg on day 1 of a 21-day cycle.

In another embodiment, if the above-noted dose combinations are not tolerated by the patient, then the dose of eribulin or the pharmaceutically acceptable salt thereof (e.g., eribulin mesylate) is reduced to 1.1 mg/m² on days 1 and 8 of a 21-day cycle (or days 1 and 15 of a 28-day cycle).

In another embodiment, if the above-noted dose combinations are not tolerated by the patient, then the dose of eribulin or the pharmaceutically acceptable salt thereof (e.g., eribulin mesylate) is reduced to 0.7 mg/m² on days 1 and 8 of a 21-day cycle (or days 1 and 15 of a 28-day cycle).

In some embodiments, the patient is selected for treatment with the combination therapy of the invention if the patient has been diagnosed with breast cancer, which optionally is metastatic breast cancer and/or triple negative breast cancer.

The present invention also provides a medicament which comprises a PD-1 antagonist as described above and a pharmaceutically acceptable excipient. When the PD-1 antagonist is a biotherapeutic agent, e.g., a mAb, the antagonist may be produced in CHO cells using conventional cell culture and recovery/purification technologies.

In some embodiments, a medicament comprising an anti-PD-1 antibody as the PD-1 antagonist may be provided as a liquid formulation or prepared by reconstituting a lyophilized powder with sterile water for injection prior to use. WO 2012/135408 describes the preparation of liquid and lyophilized medicaments comprising pembrolizumab that are suitable for use in the present invention. In some embodiments, a medicament comprising pembrolizumab is provided in a glass vial which contains about 100 mg of pembrolizumab in 4 ml of solution.

The present invention also provides a medicament which comprises eribulin or a pharmaceutically acceptable salt thereof (e.g., eribulin mesylate) and a pharmaceutically acceptable excipient.

The PD-1 antagonist and eribulin or pharmaceutically acceptable salt thereof (e.g., eribulin mesylate) medicaments described herein may be provided as a kit which comprises a first container and a second container and a package insert. The first container contains at least one dose of a medicament comprising a PD-1 antagonist, the second container contains at least one dose of a medicament comprising eribulin or a pharmaceutically acceptable salt thereof (e.g., eribulin mesylate), and the package insert, or label, which comprises instructions for treating a patient for breast cancer using the medicaments. The first and second containers may be comprised of the same or different shape (e.g., vials, syringes, and bottles) and/or material (e.g., plastic or glass). The kit may further comprise other materials that may be useful in administering the medicaments, such as diluents, filters, IV bags and lines, needles and syringes. In some preferred embodiments of the kit, the PD-1 antagonist is an anti-PD-1 antibody and the instructions state that the medicaments are intended for use in treating a patient having breast cancer that tests positive for PD-L1 expression by an IHC assay.

These and other aspects of the invention, including the exemplary specific embodiments listed below, will be apparent from the teachings contained herein.

Exemplary Specific Embodiments of the Invention

1. A method for treating breast cancer or melanoma in an individual comprising administering to the individual a combination therapy which comprises a PD-1 antagonist and eribulin or a pharmaceutically acceptable salt thereof.

2. The method of embodiment 1, wherein the PD-1 antagonist is a monoclonal antibody, or an antigen binding fragment thereof.

3. The method of embodiment 1 or 2, wherein the pharmaceutically acceptable salt of eribulin is eribulin mesylate.

4. A medicament comprising a PD-1 antagonist for use in combination with eribulin or a pharmaceutically acceptable salt thereof for treating breast cancer or melanoma in an individual, wherein the PD-1 antagonist is a monoclonal antibody, or an antigen binding fragment thereof.

5. A medicament comprising eribulin or a pharmaceutically acceptable salt thereof for use in combination with a PD-1 antagonist for treating breast cancer or melanoma in an individual.

6. The medicament of embodiment 4 or 5, which further comprises a pharmaceutically acceptable excipient.

7. Use of a PD-1 antagonist in the manufacture of medicament for treating breast cancer or melanoma in an individual when administered in combination with eribulin or a pharmaceutically acceptable salt thereof.

6. Use of eribulin or a pharmaceutically acceptable salt thereof in the manufacture of a medicament for treating breast cancer or melanoma in an individual when administered in combination with a PD-1 antagonist.

7. Use of a PD-1 antagonist and eribulin or a pharmaceutically acceptable salt thereof in the manufacture of medicaments for treating breast cancer or melanoma in an individual.

8. A kit which comprises a first container, a second container and a package insert, wherein the first container comprises at least one dose of a medicament comprising an anti-PD-1 antagonist, the second container comprises at least one dose of a medicament comprising eribulin or a pharmaceutically acceptable salt thereof, and the package insert comprises instructions for treating an individual for breast cancer using the medicaments.

9. The kit of embodiment 8, wherein the instructions state that the medicaments are intended for use in treating an individual having breast cancer that tests positive for PD-L1 expression by an immunohistochemical (IHC) assay.

10. The method, medicament, use or kit of any of embodiments 1 to 9, wherein the individual is a human and the PD-1 antagonist is a monoclonal antibody, or an antigen binding fragment thereof, which specifically binds to human PD-L1 and blocks the binding of human PD-L1 to human PD-1.

11. The method, medicament, use or kit of embodiment 9, wherein the PD-1 antagonist is MPDL3280A, BMS-936559, MEDI4736, MSB0010718C or a monoclonal antibody which comprises the heavy chain and light chain variable regions of SEQ ID NO:24 and SEQ ID NO:21, respectively, of WO2013/019906.

12. The method, medicament, use, or kit of any of embodiments 1 to 9, wherein the individual is a human, and the PD-1 antagonist is a monoclonal antibody, or an antigen binding fragment thereof, which specifically binds to human PD-1 and blocks the binding of human PD-L1 to human PD-1.

13. The method, medicament, use, or kit of embodiment 12, wherein the PD-1 antagonist also blocks binding of human PD-L2 to human PD-1.

14. The method, medicament, use or kit of embodiment 13, wherein the monoclonal antibody, or antigen binding fragment thereof, comprises: (a) light chain CDRs of SEQ ID NOs: 1, 2 and 3 and heavy chain CDRs of SEQ ID NOs: 4, 5 and 6; or (b) light chain CDRs of SEQ ID NOs: 7, 8 and 9 and heavy chain CDRs of SEQ ID NOs: 10, 11 and 12.

15. The method, medicament, use, or kit of embodiment 13, wherein the monoclonal antibody, or antigen binding fragment thereof, comprises light chain CDRs of SEQ ID NOs: 7, 8 and 9 and heavy chain CDRs of SEQ ID NOs: 10, 11, and 12.

16. The method, medicament, use, or kit of embodiment 13, wherein the PD-1 antagonist is an anti-PD-1 monoclonal antibody which comprises a heavy chain and a light chain, and wherein the heavy chain comprises SEQ ID NO: 21 and the light chain comprises SEQ ID NO: 22.

17. The method, medicament, use or kit of embodiment 13, wherein the PD-1 antagonist is an anti-PD-1 monoclonal antibody which comprises a heavy chain and a light chain, and wherein the heavy chain comprises SEQ ID NO: 23 and the light chain comprises SEQ ID NO: 24.

18. The method, medicament, use, or kit of any of embodiments 10-17, wherein the breast cancer is a solid tumor.

19. The method, medicament, use, or kit of any of embodiments 10-17, wherein the breast cancer is triple negative breast cancer.

20. The method, medicament, use, or kit of any of embodiments 10-17, wherein the breast cancer is metastatic.

21. The method, medicament, use, or kit of any of embodiments 10-17, wherein the individual has not been previously treated for breast cancer.

22. The method, medicament, use or kit of any of embodiments 10-21, the breast cancer tests positive for human PD-L1.

23. The method, medicament, use, or kit of embodiment 22, wherein the human PD-L1 expression is elevated.

25. The method, medicament, use or kit of embodiment 13, wherein the PD-1 antagonist is pembrolizumab, a pembrolizumab variant, a pembrolizumab biosimilar or nivolumab.

26. The method, medicament, use or kit of embodiment 25, wherein pembrolizumab is formulated as a liquid medicament which comprises 25 mg/ml pembrolizumab, 7% (w/v) sucrose, 0.02% (w/v) polysorbate 80 in 10 mM histidine buffer pH 5.5.

27. The method, medicament, use, or kit of any of embodiments 1 to 26, wherein the eribulin is eribulin mesylate.

28. A method for treating a human individual diagnosed with breast cancer, comprising administering to the individual a combination therapy which comprises pembrolizumab and eribulin or a pharmaceutically acceptable salt thereof, wherein the eribulin or the pharmaceutically acceptable salt thereof is administered at a dose of 1.4 mg/m$^2$, 1.1 mg/m$^2$, or 0.7 mg/m$^2$ on days 1 and 8 of a 21-day cycle and pembrolizumab is administered at a dose selected from the group consisting of 1 mg/kg Q3W, 2 mg/kg Q3W and 200 mg Q3W.

29. A medicament comprising pembrolizumab for use in combination with eribulin or a pharmaceutically acceptable salt thereof for treating breast cancer in a human individual by a method comprising administering to the individual eribulin or a pharmaceutically acceptable salt thereof at a dose of 1.4 mg/m$^2$, 1.1 mg/m$^2$, or 0.7 mg/m$^2$ on days 1 and 8 of a 21-day cycle and pembrolizumab at a dose selected from the group consisting of 1 mg/kg Q3W, 2 mg/kg Q3W and 200 mg Q3W.

30. A medicament comprising eribulin or a pharmaceutically acceptable salt thereof for use in combination with pembrolizumab for treating breast cancer in a human individual by a method comprising administering to the individual eribulin or a pharmaceutically acceptable salt thereof at a dose of 1.4 mg/m$^2$, 1.1 mg/m$^2$, or 0.7 mg/m$^2$ on days 1 and 8 of a 21-day cycle and pembrolizumab at a dose selected from the group consisting of 1 mg/kg Q3W, 2 mg/kg Q3W and 200 mg Q3W.

31. The method or medicament of any of embodiments 28 to 31, wherein the breast cancer is metastatic and/or triple negative breast cancer.

32. The method or medicament of embodiment 31, wherein the individual has not been previously treated for breast cancer.

33. The method or medicament of any of embodiments 28 to 32, wherein a tissue section of the breast cancer removed from the individual prior to administration of the combination therapy tested positive for PD-L1 expression.

34. The method or medicament of embodiment 33, wherein at least 50% of the tumor cells in the tissue section tested positive for PD-L1 expression by an immunohistochemical (IHC) assay.

35. The method or medicament of embodiment 34, wherein the IHC assay employed the antibody 22C3 to detect PD-L1 expression.

36. The method or medicament of any of embodiments 31 to 35, wherein pembrolizumab is administered by IV infusion.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000)

Monoclonal Antibodies, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14: 309-314; Barbas (1995) *Nature Medicine* 1:837-839; Mendez et al. (1997) *Nature Genetics* 15: 146-156; Hoogenboom and Chames (2000) *Immunol. Today* 21: 371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163: 5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146: 169-175; Gibellini et al. (1998) *J. Immunol.* 160: 3891-3898; Hsing and Bishop (1999) *J. Immunol.* 162: 2804-2811; Everts et al. (2002) *J. Immunol.* 168: 883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, 2nd*ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Table 3 provides a brief description of the sequences in the sequence listing.

| SEQ ID NO: | Description |
| --- | --- |
| 1 | hPD-1.08A light chain CDR1 |
| 2 | hPD-1.08A light chain CDR2 |
| 3 | hPD-1-08A light chain CDR3 |
| 4 | hPD-1.08A heavy chain CDR1 |
| 5 | hPD-1.08A heavy chain CDR2 |
| 6 | hPD-1.08A heavy chain CDR3 |
| 7 | hPD-1.09A light chain CDR1 |
| 8 | hPD-1.09A light chain CDR2 |
| 9 | hPD-1.09A light chain CDR3 |
| 10 | hPD-1.09A heavy chain CDR1 |
| 11 | hPD-1.09A heavy chain CDR2 |
| 12 | hPD-1.09A heavy chain CDR3 |
| 13 | 109A-H heavy chain variable region |
| 14 | 409A-H heavy chain full length |
| 15 | K09A-L-11 light chain variable region |
| 16 | K09A-L-16 light chain variable region |
| 17 | K09A-L-17 light chain variable region |
| 18 | K09A-L-11 light chain full length |
| 19 | K09A-L-16 light chain full length |
| 20 | K09A-L-17 light chain full length |
| 21 | Pembrolizumab Heavy chain |
| 22 | Pembrolizumab Light chain |
| 23 | Nivolumab Heavy chain |
| 24 | Nivolumab light chain |
| 25 | Human PD-L1 |

Example

Study Design

An open-label, single-arm, multicenter, Phase 1b/2 study of eribulin in combination with pembrolizumab in subjects with metastatic triple-negative breast cancer previously treated with 0 to 2 chemotherapy regimens in the metastatic setting is described below. FIG. 8 shows an example of a study design of a phase 1b/2, open label, single-arm, multicenter trial. The number of subjects provided for each phase of the study below is a non-limiting example. The particular dosing regimen and/or quantities are also non-limiting. Those of ordinary skill in the art would understand that the number of subjects participating in the study can be increased or decreased. Those of ordinary skill in the art would understand how to modify the dosing regimen and/or quantities for a particular patient or group of subjects.

A subject/patient may be included in the study if the patient has mTNBC previously treated with 0-2 lines of chemotherapy for metastatic disease. Presence of a measurable disease may be defined as ≥1 lesion of ≥10 mm in long axis diameter for nonlymph nodes or ≥15 mm in short axis diameter for lymph nodes that is serially measurable according to RECIST version 1.1 criteria. The patient may also be required to have adequate renal, bone marrow, and liver function, and a life expectancy of ≥3 months. The patient may have resolution of all chemotherapy or radiation-related toxicities to ≤grade 1 severity except for stable sensory neuropathy (grade ≤2) and alopecia (any grade).

A subject/patient may be excluded from the study if the patient has had previous treatment with eribulin or any anti-PD-1, PD-L1, or PD-L2 agent, or previous participation in a MK-3475 Merck study. A patient may be excluded if the patient has an autoimmune disease requiring treatment with systemic steroids or immunosuppressant agents, it has been less than 6 months since prior neo/adjuvant chemotherapy, and/or the patient has received treatment with chemotherapy or biological therapy within the previous 3 weeks or radiation or small-molecule targeted therapy within the previous 2 weeks. A patient may be excluded form the study if the patient has a known central nervous system disease, except for those patients with treated brain metastasis who are stable for ≥1 month, having no evidence of progression or hemorrhage after treatment and no ongoing requirement for corticosteroids, as ascertained by clinical examination and brain imaging (magnetic resonance imaging or computed tomography) during the screening period.

Subjects may have received prior neo/adjuvant chemotherapy. The Phase 1b part includes one initial safety run-in cohort in which six to twelve subjects may receive eribulin mesylate 1.4 mg/m$^2$ IV on Days 1 and 8 of a 21-day cycle and pembrolizumab 200 mg intravenously (IV) on Day 1 of a 21-day cycle (dose level 1). Eribulin may be infused over about 2-5 minutes per dose and pembrolizumab may be infused over about 25-40 minutes per dose, preferably over about 30 minutes per dose. Eribulin may be diluted in up to 100 mL of 0.9% saline for intravenous infusion.

The Phase 1b part of the study includes one initial safety run-in cohort in which at least 6 subjects may receive eribulin mesylate 1.4 mg/m$^2$ intravenously (IV) on Days 1 and 8 of a 21-day cycle and 200 mg pembrolizumab IV on Day 1 of a 21-day cycle (dose level 1). DLT may be assessed in the first cycle. Dose level 1 can be selected as the recommended Phase 2 dose (RP2D) if no more than 1 subject has a DLT. Otherwise, eribulin mesylate dose can be lowered from 1.4 mg/m$^2$ to 1.1 mg/m$^2$ on Days 1 and 8 of a 21-day cycle (dose level 0). If no more than 1 out of 6 subjects at dose level 0 has a DLT, the Phase 2 part can proceed with dose level 0. Approximately 12 subjects may be enrolled in the Phase 1b part of the study.

In the Phase 2 part, approximately 83 subjects can be enrolled in 2 strata and receive the same combination treatment at the RP2D level. The strata include no prior chemotherapy in the metastatic setting (stratum 1) and previously treated with 1 to 2 lines of chemotherapy in the metastatic setting (stratum 2). Approximately 70% and 30% of subjects may be enrolled from strata 1 and 2, respectively.

Bayesian predictive probability (PP) of response rate can be used to monitor the response rate after postbaseline tumor assessments for at least 38 subjects are available. The study could be stopped early for efficacy or futility if PP crosses the prespecified boundary. Hence, efficacy conclusion of the primary endpoint of ORR could be made on the basis of the predictive probability prior to the full enrollment of 80 evaluable subjects in the study.

Pharmacokinetic (PK) assessments of eribulin mesylate may be performed in all subjects in the Phase 1b part of the study. Subjects in the Phase 2 part may undergo sparse PK sampling for population pharmacokinetic/pharmacodynamic (PK/PD) analysis where feasible.

Study Treatments.

Combination doses can be investigated in one cohort. Eribulin mesylate 1.4 mg/m$^2$ via IV injection over 2 to 5 minutes administered on Day 1 and Day 8 and 200 mg pembrolizumab via IV infusion over 30 minutes administered on Day 1 (21-day cycle). Alternative doses may be explored to identify the RP2D prior to the start of the Phase 2 part if necessary. The eribulin mesylate dose may be reduced/delayed; the pembrolizumab dose may be delayed per protocol in the event of toxicity. Dose delays and modifications for toxicities associated with eribulin mesylate and pembrolizumab are described in detail below.

Duration of Treatment.

Subjects may be treated with eribulin mesylate and pembrolizumab and can remain on one or both study drugs in the presence of clinical benefit until intercurrent illness, unacceptable toxicity, or disease progression occurs, or until the subject withdraws consent.

Efficacy Analyses

Primary Efficacy Phase 1b.

The study can include at least one safety run-in cohort in which six metastatic mTNBC subjects who receive eribulin mesylate 1.4 mg/m$^2$ on Days 1 and 8 and 200 mg pembrolizumab on Day 1 of a 21-day cycle (dose level 1). Subjects may be observed for dose-limiting toxicity in the first cycle. The purpose of the safety run-in cohort(s) is to study safety of the 2-drug combination. The Phase 2 part may proceed with dose level 1 when no more than one subject has a DLT. Otherwise, a lower eribulin mesylate dose of 1.1 mg/m$^2$ and 200 mg pembrolizumab can be evaluated in another cohort of six subjects (dose level 0). If no more than 1 subject has a DLT, the Phase 2 part will proceed with dose level 0 as the RP2D. Otherwise, alternative doses (eribulin mesylate 0.7 mg/m$^2$) may be explored prior to the start of the Phase 2 part.

Primary Efficacy Phase 2.

Bayesian predictive probability (PP) can be used to monitor the response rate after post baseline tumor assessments of at least 38 subjects are available. The calculation of PP is based on the goal of claiming superiority of the combination at the end of the study if $$P(p>0.2|\text{data}) \geq 0.95 \qquad \text{(Eqn. 1)}$$

where p is the response rate of the combination, 0.2 is the response rate of historical control, based on single-agent pembrolizumab and eribulin mesylate in recent trials; 0.95 is the prespecified target probability ($\theta_T$) and $P(p>0.2|\text{data})$ is the posterior probability. On the basis of the accumulated data so far in the study, the probabilities of all possible future outcomes that lead to equation (1) at the end of the study may be added in order to obtain the predictive probability of the efficacy of the combination. Therefore, early determination is possible for claiming the combination efficacious when PP is above a prespecified upper threshold ($\theta_U$) or for claiming futility when PP is below a prespecified lower threshold ($\theta_L$). The upper and lower cutoff probabilities for decision-making, $\theta_U$ and $\theta_L$, are set as 0.99 and 0.025. Under the predictive monitoring, the study can proceed as follows:

If PP>$\theta_U$(=0.99), stop the study and claim the combination efficacious or promising;

If PP<$\theta_L$(=0.025), stop the study and claim the combination not promising; Otherwise, continue the study until the number of evaluable subjects reaches to 80.

The Bayesian stopping boundaries are included in Table 4 below. During the study, PP may be calculated with updated response information until the boundary is crossed. In case continuous PP monitoring is not conducted because of operational and logistic reasons (e.g., delayed tumor assessments and fast enrollment) or it is decided to take the study to full enrollment in order to gather more efficacy data, posterior probability in equation (1) may be evaluated to determine the efficacy of the combination regimen after the tumor response status has been collected from the last evaluable subjects. That is, to claim efficacy if P (p>0.2 |data)≥0.95. A 2-sided 95% credible interval of objective response rate in the evaluable subjects may be constructed to aid the interpretation of the results.

TABLE 4

Bayesian stopping boundaries

| N | LB | UB |
|---|----|----|
| 38 | 6 | 16 |
| 39 | 7 | 16 |
| 40 | 7 | 17 |
| 41 | 7 | 17 |
| 42 | 8 | 17 |
| 43 | 8 | 17 |
| 44 | 8 | 18 |
| 45 | 8 | 18 |
| 46 | 9 | 18 |
| 47 | 9 | 18 |
| 48 | 9 | 19 |
| 49 | 10 | 19 |
| 50 | 10 | 19 |
| 51 | 10 | 19 |
| 52 | 10 | 20 |
| 53 | 11 | 20 |
| 54 | 11 | 20 |
| 55 | 11 | 20 |
| 56 | 12 | 20 |
| 57 | 12 | 21 |
| 58 | 12 | 21 |
| 59 | 13 | 21 |
| 60 | 13 | 21 |
| 61 | 13 | 21 |
| 62 | 14 | 22 |
| 63 | 14 | 22 |
| 64 | 14 | 22 |
| 65 | 15 | 22 |
| 66 | 15 | 22 |
| 67 | 15 | 22 |
| 68 | 16 | 23 |
| 69 | 16 | 23 |
| 70 | 17 | 23 |
| 71 | 17 | 23 |
| 72 | 17 | 23 |
| 73 | 18 | 23 |
| 74 | 18 | 23 |
| 75 | 19 | 23 |
| 76 | 19 | 23 |
| 77 | 20 | 23 |
| 78 | 20 | 23 |
| 79 | 21 | 23 |
| 80 | 22 | 23 |

N = number
LB = lower bound
UB = upper bound

Tumor assessment can be performed based on, for example, RECIST 1.1 and irRC. Efficacy can be evaluated by objective tumor responses provided by the investigator according to Response Evaluation Criteria in Solid Tumors (RECIST [version 1.1]) for use in the analysis of primary endpoint (ORR), secondary endpoints (PFS and DOR), and an exploratory endpoint (clinical benefit rate (CBR)). Tumor assessments can be performed every 9 weeks±1 week using consistent imaging methodology (i.e., CT scan/MRI or bone scan) and consistent use or nonuse of contrast media). In the exploratory analyses, clinical activity for the combination treatment including ORR, PFS, DOR, and CBR may also be evaluated using the irRC. In addition, OS status (disposition) may be assessed throughout the study.

Primary Efficacy Final Analysis.

While it is possible to determine the efficacy of the combination regimen in terms of ORR early in the study to aid quick decision-making, the final analysis may be performed after all ongoing subjects complete at least 24 weeks of treatment, or discontinue from treatment, and at least 75% subjects have disease progression or death event. Primary, secondary, and exploratory endpoints may be summarized overall and by cohorts. Subjects in the Phase 1b part who were treated at the phase 2 dosing regimen and who were deemed evaluable may be combined with Phase 2 subjects in the efficacy analysis.

Secondary Efficacy

Progression-free survival (PFS), OS, and DOR can be analyzed using Kaplan-Meier product-limit estimates. Median PFS and OS and the cumulative probability of PFS, OS, and DOR at 6 and 12 months can be presented with 2-sided 95% confidence intervals (CIs) if estimable. The cumulative PFS, OS, and DOR can be plotted over time. The median and first and third quartiles from Kaplan-Meier estimation for PFS, OS, and DOR may be provided with 95% CIs if estimable. The primary and secondary efficacy endpoints (i.e., ORR, PFS, OS, and DOR) can be further evaluated in the PD-L1 Positive Set after a cutoff point is determined with external data. The clinical utility of PD-L1 as a predictive marker in mTNBC subjects who receive eribulin and pembrolizumab combination treatment can be assessed.

Treatments Administered.

Eribulin mesylate and pembrolizumab can be administered as described in Table 5.

TABLE 5

Treatments administered

| Drug Name | Dose | Dose Form | Infusion Rate | Day/Cycle |
|-----------|------|-----------|---------------|-----------|
| Eribulin Mesylate | 1.4 mg/m$^2$ | IV infusion | Infused over 2-5 minutes | Day 1 and Day 8 of each 21-day cycle |
| Pembrolizumab | 200 mg | IV infusion | Infused over 30 minutes (−5 min/+10 min range allowed) | Day 1 of each 21-day cycle |

The amount of eribulin mesylate (as calculated above) can be withdrawn from the appropriate number of vials into a syringe. This may be administered directly as an intravenous injection over 2 to 5 minutes or diluted in up to 100 mL 0.9% saline for IV infusion over 2 to 5 minutes. No special tubing is required for IV administration of eribulin mesylate.

Pembrolizumab may be administered up to 3 days before or after the scheduled Day 1 of each cycle. When the 2 study drugs are scheduled to be administrated simultaneously on Day 1 of each 21-day cycle, pembrolizumab can be given first and followed by eribulin mesylate. Subjects initially treated with eribulin mesylate and pembrolizumab can remain on one or both study drugs in the presence of clinical benefit until intercurrent illness, unacceptable toxicity, or disease progression occurs, or until the subject withdraws consent. In the event of an AE leading to treatment interruption or delay of either study drug, the subject may continue treatment with the other study drug, as long as there is a clinical benefit.

Eribulin mesylate dose may be reduced/delayed during the study. Dose interruption and dose reduction instructions for subjects who experience eribulin toxicity are presented in Table 6:

TABLE 6

Eribulin Mesylate Dose Adjustments for Toxicity

| Adverse Reaction/Toxicity[a] | Eribulin Mesylate Dose Modification |
|---|---|
| Hematologic: | |
| ANC <500 cells/mm$^3$ lasting >7 days in the previous cycle despite use of growth factors, recovered to Grade ≤2 | 1.1 mg/m$^2$ |
| ANC <1,000 cells/mm$^3$ complicated by fever or infection despite use of growth factors, recovered to Grade <2 | 1.1 mg/m$^2$ |
| Nonhematologic[b]: | |
| Grade 3 or 4 event in the previous cycle, recovered to Grade <2 | 1.1 mg/m$^2$ |

TABLE 6-continued

Eribulin Mesylate Dose Adjustments for Toxicity

| Adverse Reaction/Toxicity[a] | Eribulin Mesylate Dose Modification |
|---|---|
| Recurrence of any Grade 3 or 4 event despite reduction to 1.1 mg/m$^2$ | 0.7 mg/m$^2$ |
| Recurrence of any Grade 3 or 4 event despite reduction to 0.7 mg/m$^2$ | Consider discontinuation of combination treatment |

ANC = absolute neutrophil count.
[a]Toxicities graded in accordance with National Cancer Institute Common Terminology Criteria for Adverse Events, Version 4.03 (NCI-CTCAE, v 4.03).
[b]Eribulin mesylate related.

As an example of dose delay, eribulin may not be administered in the event of any of the following: (1) absolute neutrophil count ("ANC")<1000, (2) platelets <75,000/mm$^3$, and/or (3) Grade 3 or 4 nonhematological toxicities. Eribulin Day 8 dose may be delayed for a maximum of up to 7 additional days (total of 15 days). If toxicities do not resolve or improve to ≤Grade 2 severity by Day 15, the Erubulin Day 8 dose may be omitted and the next cycle may not be initiated until at least two weeks later than the Day 8. If a dose is delayed for toxicities wherein the patient later recovered to Grade 2 severity or less, then administration of eribulin may resume at a reduced dose as set out in the above table.

Pembrolizumab may not be subject to dose reductions. The dose of pembrolizumab may be delayed because of an adverse event. Adverse events, both nonserious and serious, associated with pembrolizumab exposure may represent an immunologic etiology. These adverse events may occur shortly after the first dose or several months after the last dose or treatment. For drug-related toxicities and severe or life-threatening AEs that occur soon after a pembrolizumab dose, pembrolizumab must be withheld or discontinued per Table 7:

TABLE 7

Dose Modification Guidelines for Pembrolizumab-Related Adverse Events

| Toxicity | Hold Treatment For Grade | Timing for Restarting Treatment | Treatment Discontinuation |
|---|---|---|---|
| Diarrhea/Colitis | 2-3 | Toxicity resolves to Grade 0-1. | Toxicity does not resolve within 12 weeks of last dose or inability to reduce corticosteroid to 10 mg or less of prednisone or equivalent per day within 12 weeks. |
|  | 4 | Permanently discontinue. | Permanently discontinue. |
| AST, ALT, or Increased Bilirubin | 2 | Toxicity resolves to Grade 0-1. | Toxicity does not resolve within 12 weeks of last dose. |
|  | 3-4 | Permanently discontinue (see exception below).[a] | Permanently discontinue. |
| Type 1 diabetes mellitus (if new onset) or Hyperglycemia | T1DM or 3-4 | Hold pembrolizumab for new onset Type 1 diabetes mellitus or Grade 3-4 hyperglycemia associated with evidence of beta cell failure. | Resume pembrolizumab when subjects are clinically and metabolically stable. |

TABLE 7-continued

Dose Modification Guidelines for Pembrolizumab-Related Adverse Events

| Toxicity | Hold Treatment For Grade | Timing for Restarting Treatment | Treatment Discontinuation |
|---|---|---|---|
| Hypophysitis | 2-4 | Toxicity resolves to Grade 0-1. Treatment with pembrolizumab can be continued while endocrine replacement therapy is instituted. | Toxicity does not resolve within 12 weeks of last dose or inability to reduce corticosteroid to 10 mg or less of prednisone or equivalent per day within 12 weeks. |
| Hyperthyroidism | 3 | Toxicity resolves to Grade 0-1. | Toxicity does not resolve within 12 weeks of last dose or inability to reduce corticosteroid to 10 mg or less of prednisone or equivalent per day within 12 weeks. |
| Hypothyroidism | 4 | Permanently discontinue. Treatment with pembrolizumab can be continued while thyroid replacement therapy is instituted. | Permanently discontinue. Treatment with pembrolizumab can be continued while thyroid replacement therapy is instituted. |
| Infusion Reaction | 3-4 | Permanently discontinue. | Permanently discontinue. |
| Pneumonitis | 2 | Toxicity resolves to Grade 0-1. | Toxicity does not resolve within 12 weeks of last dose or inability to reduce corticosteroid to 10 mg or less of prednisone or equivalent per day within 12 weeks. |
| | 3-4 | Permanently discontinue. | Permanently discontinue. |
| Renal Failure or Nephritis | 2 | Toxicity resolves to Grade 0-1 | Toxicity does not resolve within 12 weeks of last dose or inability to reduce corticosteroid to 10 mg or less of prednisone or equivalent per day within 12 weeks. |
| | 3-4 | Permanently discontinue. | Permanently discontinue. |
| All Other Drug-Related Toxicity[b] | 3 or Severe | Toxicity resolves to Grade 0-1. | Toxicity does not resolve within 12 weeks of last dose or inability to reduce corticosteroid to 10 mg or less of prednisone or equivalent per day within 12 weeks. |
| | 4 | Permanently discontinue. | Permanently discontinue. |

AE = adverse event,
ALT = alanine aminotransferase,
AST = aspartate aminotransferase
Note:
Permanently discontinue for any severe or Grade 3 drug-related adverse event (AE) that recurs or for any life-threatening event.
[a]For subjects with liver metastasis who begin treatment with Grade 2 AST or ALT, if AST or ALT increases by greater than or equal to 50% relative to baseline and lasts for at least 1 week, then subjects should be discontinued.
[b]Subjects with an intolerable or persistent Grade 2 drug-related AE may have study drug held at the physician's discretion. Permanently discontinue study drug for persistent Grade 2 adverse reactions (except for alopecia and peripheral sensory neuropathy for which treatment with study drug has been held) that do not recover to Grade 0-1 within 12 weeks of the last dose.

Treatment/End of Treatment Assessments

Dose-limiting toxicity (DLT) assessments can be conducted for Phase 1b subjects. DLTs include Hematologic Toxicities such as any Grade 4 thrombocytopenia or neutropenia lasting >7 days, and Nonhematologic Toxicities including:

Episcleritis, uveitis, or iritis of Grade 2 or higher
Any Grade 4 toxicity
Any Grade 3 toxicity EXCLUDING:
    Nausea/vomiting/diarrhea controlled by medical intervention within 72 hours
    Grade 3 rash in the absence of desquamation, no mucosal involvement, does not require steroids, and resolves to Grade 1 by the next scheduled dose of pembrolizumab
    Transient Grade 3 AST or ALT elevation, defined as no more than 3 days with or without steroid use
Discontinuation or delay of more than 2 weeks of either study medication due to treatment-related AE can be considered as a DLT Subjects enrolled in Phase 1b can be assessed for DLTs during a DLT assessment window of the first cycle of 21 days. Subjects who discontinue study treatment prior to completing the DLT assessment window for any reason other than a DLT may be replaced.

Safety assessments can include monitoring and recording of adverse events (AE) throughout the study, including Common Terminology Criteria for Adverse Events v4.03 grades for both increasing and decreasing severity and serious adverse events; regular monitoring of hematology, clinical chemistry, and urine; periodic measurement of vital signs; and performance of physical examinations. Physical examination and laboratory evaluation for hematology can be performed at baseline (day 1) and day 8 of each treatment cycle, and within 30 days of the final treatment. Laboratory evaluation for chemistry can be performed at baseline (day 1) and within 30 days of the final treatment. Thyroid function will be assessed at the screening visit and then every 2 cycles throughout the study.

Study Endpoints

Primary Endpoint.

The primary endpoints are safety and tolerability (based on RECIST Version 1.1) for the phase 1b part of the study and objective response rate for the phase 2 part of the study (ORR). ORR is defined as the proportion of subjects who had a BOR of CR or PR.

Secondary Endpoints.

The secondary endpoints of the study are progression-free survival, overall survival, duration of response, and efficacy in a subset of patients defined by PD-L1 expression.

Progression-Free Survival (PFS)—defined as the time from date of first dose of study drug to date of first documentation of disease progression or death, whichever occurs first Overall Survival (OS)—defined as the time from the date of first dose of study drug until date of death from any cause Duration of Response (DOR)—defined as the time from the date that a confirmed objective response is first documented to the date of PD or death due to any cause for those subjects with a confirmed PR or CR.

REFERENCES

1. Sharpe, A. H, Wherry, E. J., Ahmed R., and Freeman G. J., The function of programmed cell death 1 and its ligands in regulating autoimmunity and infection. *Nature Immunology* (2007); 8: 239-245.
2. Dong H et al., Tumor-associated B7-H1 promotes T-cell apoptosis: a potential mechanism of immune evasion. *Nat Med.* 2002 August; 8(8): 793-800.
3. Yang et al., PD-1 interaction contributes to the functional suppression of T-cell responses to human uveal melanoma cells in vitro. *Invest Ophthalmol Vis Sci.* 2008 June; 49(6 (2008): 49: 2518-2525.
4. Ghebeh et al., The B7-H1 (PD-L1) T lymphocyte-inhibitory molecule is expressed in breast cancer patients with infiltrating ductal carcinoma: correlation with important high-risk prognostic factors. *Neoplasia* (2006) 8: 190-198.
5. Hamanishi J et al., Programmed cell death 1 ligand 1 and tumor-infiltrating CD8+ T lymphocytes are prognostic factors of human ovarian cancer. *Proceeding of the National Academy of Sciences* (2007): 104: 3360-3365.
6. Thompson R H et al., Significance of B7-H1 overexpression in kidney cancer. *Clinical genitourin Cancer* (2006): 5: 206-211.
7. Nomi, T. Sho, M., Akahori, T., et al., Clinical significance and therapeutic potential of the programmed death-1 ligand/programmed death-1 pathway in human pancreatic cancer. *Clinical Cancer Research* (2007); 13: 2151-2157.
8. Ohigashi Y et al., Clinical significance of programmed death-1 ligand-1 and programmed death-1 ligand 2 expression in human esophageal cancer. *Clin. Cancer Research* (2005): 11: 2947-2953.
9. Inman et al., PD-L1 (B7-H1) expression by urothelial carcinoma of the bladder and BCG-induced granulomata: associations with localized stage progression. *Cancer* (2007): 109: 1499-1505.
10. Shimauchi T et al., Augmented expression of programmed death-1 in both neoplasmatic and nonneoplastic CD4+ T-cells in adult T-cell Leukemia/Lymphoma. *Int. J. Cancer* (2007): 121: 2585-2590.
11. Gao et al., Overexpression of PD-L1 significantly associates with tumor aggressiveness and postoperative recurrence in human hepatocellular carcinoma. *Clinical Cancer Research* (2009) 15: 971-979.
12. Nakanishi J., Overexpression of B7-H1 (PD-L1) significantly associates with tumor grade and postoperative prognosis in human urothelial cancers. *Cancer Immunol Immunother.* (2007) 56: 1173-1182.
13. Hino et al., Tumor cell expression of programmed cell death-1 is a prognostic factor for malignant melanoma. *Cancer* (2010): 00: 1-9.
14. Ghebeh H., Foxp3+ tregs and B7-H1+/PD-1+ T lymphocytes co-infiltrate the tumor tissues of high-risk breast cancer patients: implication for immunotherapy. *BMC Cancer.* 2008 Feb. 23; 8:57.
15. Ahmadzadeh M. et al., Tumor antigen-specific CD8 T cells infiltrating the tumor express high levels of PD-1 and are functionally impaired. *Blood* (2009) 114: 1537-1544.
16. Thompson R H et al., PD-1 is expressed by tumor infiltrating cells and is associated with poor outcome for patients with renal carcinoma. *Clinical Cancer Research* (2007) 15: 1757-1761.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The invention claimed is:

1. A method for treating triple negative breast cancer in an individual comprising administering to the individual a combination therapy which comprises (i) an antagonist of a Programmed Death 1 protein (PD-1), wherein the PD-1 antagonist is pembrolizumab, and (ii) eribulin or a pharmaceutically acceptable salt thereof.

2. The method of claim 1, wherein the individual is a human.

3. The method of claim 1, wherein the triple negative breast cancer is metastatic.

4. The method of claim 1, wherein the pharmaceutically acceptable salt of eribulin is eribulin mesylate.

5. The method of claim 1, wherein the eribulin or the pharmaceutically acceptable salt thereof is administered at a dose of 1.4 mg/m2, 1.1 mg/m2, or 0.7 mg/m2 on days 1 and 8 of a 21-day cycle, wherein the pembrolizumab is administered at a dose of 200 mg Q3W.

6. The method of claim 1, wherein the cancer tests positive for PD-L1 expression by an immunohistochemical assay.

* * * * *

SEQUENCE LISTING

<160> NUMBER OF SEQ ID NOS: 25

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 1

Arg Ala Ser Lys Ser Val Ser Thr Ser Gly Phe Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 2

Leu Ala Ser Asn Leu Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 3

Gln His Ser Trp Glu Leu Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Antibody
      Heavy Chain CDR

<400> SEQUENCE: 4

Ser Tyr Tyr Leu Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Antibody
      Heavy Chain CDR

<400> SEQUENCE: 5

Gly Val Asn Pro Ser Asn Gly Gly Thr Asn Phe Ser Glu Lys Phe Lys
1               5                   10                  15

Ser

<210> SEQ ID NO 6
<211> LENGTH: 11
<212> TYPE: PRT
<213> ORGANISM: Artificial Sequence

```
<220> FEATURE:
<223> OTHER INFORMATION: Description of Artificial Sequence: Antibody
      Heavy Chain CDR

<400> SEQUENCE: 6

Arg Asp Ser Asn Tyr Asp Gly Gly Phe Asp Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 7

Arg Ala Ser Lys Gly Val Ser Thr Ser Gly Tyr Ser Tyr Leu His
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 8

Leu Ala Ser Tyr Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Antibody
      Light Chain CDR

<400> SEQUENCE: 9

Gln His Ser Arg Asp Leu Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Antibody
      Heavy Chain CDR

<400> SEQUENCE: 10

Asn Tyr Tyr Met Tyr
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Antibody
      Heavy Chain CDR
```

```
<400> SEQUENCE: 11

Gly Ile Asn Pro Ser Asn Gly Gly Thr Asn Phe Asn Glu Lys Phe Lys
1               5                   10                  15

Asn

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Antibody
      Heavy Chain CDR

<400> SEQUENCE: 12

Arg Asp Tyr Arg Phe Asp Met Gly Phe Asp Tyr
1               5                   10

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Humanized
      Antibody Heavy Chain Variable Region

<400> SEQUENCE: 13

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 14
<211> LENGTH: 447
<212> TYPE: PRT
<213> ORGANISM: Artificial Sequence
<220> FEATURE:
<223> OTHER INFORMATION: Description of Artificial Sequence: Humanized
      Antibody Heavy Chain

<400> SEQUENCE: 14

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60
```

```
Lys Asn Arg Val Thr Leu Thr Thr Asp Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 15
<211> LENGTH: 111
<212> TYPE: PRT
<213> ORGANISM: Artificial Sequence
```

<220> FEATURE:
<223> OTHER INFORMATION: Description of Artificial Sequence: Humanized
    Antibody Light Chain Variable Region

<400> SEQUENCE: 15

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Humanized
    Antibody Light Chain Variable Region

<400> SEQUENCE: 16

```
Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys
            100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Humanized
    Antibody Light Chain Variable Regon

<400> SEQUENCE: 17

```
Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45
```

```
Gln Leu Leu Ile Tyr Leu Ala Ser Tyr Leu Glu Ser Gly Val Pro Asp
 50                  55                  60

Arg Phe Ser Gly Ser Gly Ser Gly Thr Ala Phe Thr Leu Lys Ile Ser
 65                  70                  75                  80

Arg Val Glu Ala Glu Asp Val Gly Leu Tyr Tyr Cys Gln His Ser Arg
                 85                  90                  95

Asp Leu Pro Leu Thr Phe Gly Gln Gly Thr Lys Leu Glu Ile Lys
            100                 105                 110
```

```
<210> SEQ ID NO 18
<211> LENGTH: 218
<212> TYPE: PRT
<213> ORGANISM: Artificial Sequence
<220> FEATURE:
<223> OTHER INFORMATION: Description of Artificial Sequence: Humanized
      Antibody Light Chain

<400> SEQUENCE: 18

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Lys Gly Val Ser Thr Ser
                 20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Humanized
      Antibody Light Chain
```

<400> SEQUENCE: 19

```
Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 218
<212> TYPE: PRT
<213> ORGANISM: Artificial Sequence
<220> FEATURE:
<223> OTHER INFORMATION: Description of Artificial Sequence: Humanized
      Antibody Light Chain

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<223> OTHER INFORMATION: Description of Artificial Sequence: Humanized
      Antibody Heavy Chain

<400> SEQUENCE: 21

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

```
Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 22
<211> LENGTH: 218
<212> TYPE: PRT
<213> ORGANISM: Artificial Sequence
<220> FEATURE:
<223> OTHER INFORMATION: Description of Artificial Sequence: Humanized
      Antibody Light Chain

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 23
<211> LENGTH: 440
<212> TYPE: PRT
<213> ORGANISM: Homo sapiens

<400> SEQUENCE: 23

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

```
Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 24
<211> LENGTH: 214
<212> TYPE: PRT
<213> ORGANISM: Homo sapiens

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 290
<212> TYPE: PRT
<213> ORGANISM: Homo sapiens
<220> FEATURE:
<221> NAME/KEY: mat_peptide
<222> LOCATION: (19)..(290)
```

```
<400> SEQUENCE: 25

Met Arg Ile Phe Ala Val Phe Ile Phe Met Thr Tyr Trp His Leu Leu
            -15             -10                   -5

Asn Ala Phe Thr Val Thr Val Pro Lys Asp Leu Tyr Val Val Glu Tyr
     -1  1            5                   10

Gly Ser Asn Met Thr Ile Glu Cys Lys Phe Pro Val Glu Lys Gln Leu
 15              20                  25                      30

Asp Leu Ala Ala Leu Ile Val Tyr Trp Glu Met Glu Asp Lys Asn Ile
             35                  40                  45

Ile Gln Phe Val His Gly Glu Glu Asp Leu Lys Val Gln His Ser Ser
             50                  55                  60

Tyr Arg Gln Arg Ala Arg Leu Leu Lys Asp Gln Leu Ser Leu Gly Asn
         65              70                  75

Ala Ala Leu Gln Ile Thr Asp Val Lys Leu Gln Asp Ala Gly Val Tyr
         80              85                  90

Arg Cys Met Ile Ser Tyr Gly Gly Ala Asp Tyr Lys Arg Ile Thr Val
 95              100                 105                     110

Lys Val Asn Ala Pro Tyr Asn Lys Ile Asn Gln Arg Ile Leu Val Val
             115                 120                 125

Asp Pro Val Thr Ser Glu His Glu Leu Thr Cys Gln Ala Glu Gly Tyr
             130                 135                 140

Pro Lys Ala Glu Val Ile Trp Thr Ser Ser Asp His Gln Val Leu Ser
             145                 150                 155

Gly Lys Thr Thr Thr Thr Asn Ser Lys Arg Glu Glu Lys Leu Phe Asn
     160                 165                 170

Val Thr Ser Thr Leu Arg Ile Asn Thr Thr Thr Asn Glu Ile Phe Tyr
 175                 180                 185                 190

Cys Thr Phe Arg Arg Leu Asp Pro Glu Glu Asn His Thr Ala Glu Leu
             195                 200                 205

Val Ile Pro Glu Leu Pro Leu Ala His Pro Pro Asn Glu Arg Thr His
             210                 215                 220

Leu Val Ile Leu Gly Ala Ile Leu Leu Cys Leu Gly Val Ala Leu Thr
             225                 230                 235

Phe Ile Phe Arg Leu Arg Lys Gly Arg Met Met Asp Val Lys Lys Cys
             240                 245                 250

Gly Ile Gln Asp Thr Asn Ser Lys Lys Gln Ser Asp Thr His Leu Glu
 255                 260                 265                 270

Glu Thr
```